United States Patent [19]

Ishikawa et al.

[11] Patent Number: 5,494,897
[45] Date of Patent: Feb. 27, 1996

[54] ENDOTHELIN ANTAGONISTIC PEPTIDE

[75] Inventors: Kiyofumi Ishikawa; Takehiro Fukami; Masaki Ihara; Mitsuo Yano, all of Tsukuba, Japan

[73] Assignee: Banyu Pharmaceutical Co., Ltd., Tokyo, Japan

[21] Appl. No.: 253,775

[22] Filed: Jun. 3, 1994

[30] Foreign Application Priority Data

Jun. 3, 1993 [JP] Japan ................................. 5-157907

[51] Int. Cl.⁶ ......................... A61K 38/00; A61K 38/04; C07K 5/00
[52] U.S. Cl. ..................... 514/18; 514/19; 530/330; 530/331
[58] Field of Search ................. 514/18, 19; 530/330, 530/331

[56] References Cited

U.S. PATENT DOCUMENTS 5,144,918  5/1992  Ishikawa et al. .

FOREIGN PATENT DOCUMENTS 0436189  7/1991  European Pat. Off. .
0460679  12/1991  European Pat. Off. .

OTHER PUBLICATIONS

Tetrahedron Letters, vol. 33, No. 1, 1992, pp.29–32, Rajesh K. Dua, et al., "Synthesis of 5–Cyano–L–Tryptophan".

*Primary Examiner*—Jill Warden
*Assistant Examiner*—Benet Prickril
*Attorney, Agent, or Firm*—Oblon, Spivak, McClelland, Maier & Neustadt

[57] ABSTRACT

A peptide derivative of the formula:

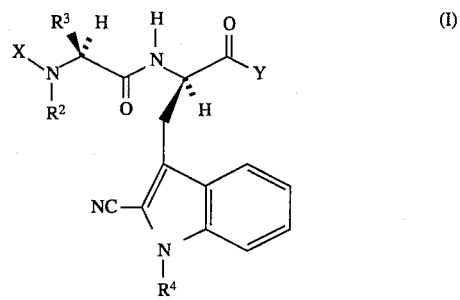

is a novel compound having antagonism against three endothelin isopeptides. A 2-cyanotryptophan or a protected compound thereof, is an intermediate for the preparation of the endothelin antagonist.

8 Claims, No Drawings

ENDOTHELIN ANTAGONISTIC PEPTIDE

BACKGROUND OF THE INVENTION

1. Field of the Invention

The present invention relates to novel compounds having antagonism against three endothelin isopeptides (endothelin-1, endothelin-2 and endothelin-3), which are physiologically highly active endogenous peptides, processes for their preparation and their use as a drug, and 2-cyanotryptophan or a protected compound thereof which is a key intermediate for preparing the above-mentioned novel endothelin antagonistic compounds.

2. Discussion of Background

Two endothelin receptor subtypes $ET_A$ and $ET_B$ are known so far. The compounds of the present invention possess high affinity to at least the $ET_B$ receptors, thereby inhibiting vasoconstriction and bronchoconstriction induced by the endothelins. The compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, endotoxin shock, endotoxin-induced multiple organ failure or disseminated intravascular coagulation, and/or cyclosporin-induced renal failure or hypertension.

Endothelin is a polypeptide composed of 21 amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, U.S.A., 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular Medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, Invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane A2, prostacyclin, noradrenaline, angiotensin II and substance P (Biochem. Biophys, Res. Commun., 157, 1164–1168 (1988); Biochem. Biophys, Res. Commun., 155, 167–172 (1989); Proc. Natl. Acad. Sci. U.S.A., 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)). Further, it was reported that cyclosporin remarkably increased endothelin secretion in the renal cell culture (LLC-PK1 cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, $R^856$–$R^866$ (1989)).

It is known that vasoconstriction by the endothelins is caused via at least two subtypes of endothelin receptors (J. Cardiovasc. Pharmacol., 17(Suppl.7), S119–S121 (1991)). One of endothelin receptors is $ET_A$ receptor selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. The present inventors already disclosed potent endothelin $ET_A$ receptor antagonists in EP 0460679A2 and EP 0436189A1. Since, the action of the endothelins is caused via not only the $ET_A$ receptor but also the $ET_B$ receptor, novel substances with $ET_B$ receptor antagonistic activity are desired to block activities of the endothelins in various diseases.

Endothelin is an endogenous substance which directly or indirectly (by controlling liberation of various endogenous substances) induces sustained contraction of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, acute renal failure, myocardial infarction, angina pectoris, cerebral vasospasm and cerebral infarction. Further, it is suggested that endothelin serves as an important mediator involved in disease such as endotoxin shock, endotoxin-induced multiple organ failure or disseminated intravascular coagulation, and/or cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. Accordingly, it is an object of the present invention to provide a novel therapeutics for the treatment of the above-mentioned various diseases by an invention of a potent $ET_B$ receptor antagonist.

In order to accomplish the above object, the present inventors have synthesized various peptide derivatives and have investigated their endothelin antagonistic activities, and as a result have found that novel peptide derivatives represented by the following formula (I) and their pharmaceutically acceptable salts have strong potent $ET_B$ receptor antagonistic activities. The present invention has been accomplished on the basis of this discovery.

Thus, the present invention provides a peptide derivative of the formula:

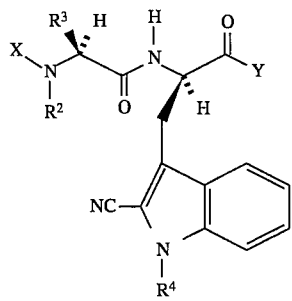
(I)

wherein $R^2$ is a hydrogen atom or a lower alkyl group; $R^3$ is a lower alkyl group which is unsubstituted or substituted with a lower alkylthio group, a lower alkenyl group, a cycloalkyl group or a cycloalkyl lower alkyl group wherein optional one to four hydrogen atoms on the ring may independently be replaced by a lower alkyl group, an aryl group, a heteroaryl group, an aryl lower alkyl group or a heteroaryl lower alkyl group; $R^4$ is a hydrogen atom, a lower alkyl group or an acyl group; X and Y are mutually dependent; when X is a group of the formula $R^{11}$—O—C(=O) or a group of the formula $R^{12}R^{13}N$—C(=O), Y is a group of the formula:

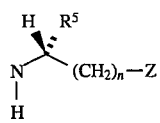
(II)

wherein $R^{11}$ is a lower alkyl group or an aryl group, $R^{12}$ is a lower alkyl group, a cycloalkyl group, a cycloalkyl lower alkyl group, a 1-adamantyl group, or an aryl group or a heteroaryl group wherein optional one or two hydrogen atoms on the ring may independently be replaced by an optional group selected from the group consisting of a lower alkyl group, a lower alkoxy group, a halogen atom, a trifluoromethyl group, a nitro group, an amino group and a formyl amino group, $R^{13}$ is a hydrogen atom, a lower alkyl group which is unsubstituted or substituted with a hydroxyl group, a cycloalkyl group or a cycloalkyl lower alkyl group, or $R^{12}$ and $R^{13}$ form, together with the adjacent nitrogen atom, a 5- to 9-membered nitrogen-containing saturated heterocyclic ring having 4 to 8 carbon atoms (wherein among methylene groups forming the ring, optional one methylene group may be replaced by a thio group, optional one to four hydrogen atoms on the carbon atoms of the heterocyclic ring may independently be replaced by a lower alkyl group or a hydroxy lower alkyl group, and further two adjacent carbon atoms in the heterocyclic ring may form a benzo-fused ring), $R^5$ is a hydrogen atom, or a lower alkyl group or a lower alkenyl group which may have one to three substituents selected from the group consisting of a hydroxyl group, a lower alkoxy group, a lower alkylthio group, an aryl group and a heteroaryl group, n is 0 or 1, Z is a hydroxymethyl group, a group of the formula $CO_2R^{61}$ (wherein $R^{61}$ is a hydrogen atom or a lower alkyl group ), a group of the formula $CONR^{62}R^{63}$ (wherein each of $R^{62}$ and $R^{63}$ is independently a hydrogen atom, an aryl group, a heteroaryl group, or a lower alkyl group which may have one to three substituents selected from the group consisting of a hydroxyl group, a carboxyl group and a sulfo group), a 1H-tetrazol-5-yl group, a sulfo group or a phosphono group, and when X is a group of the formula:

(III)

, Y is a group of the formula:

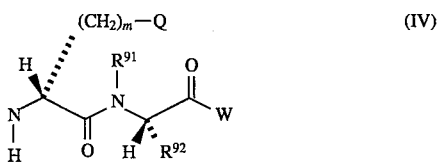
(IV)

wherein $R^{71}$ is a hydrogen atom, $R^{72}$ is a lower alkyl group which is unsubstituted or substituted with a lower alkylthio group, a cycloalkyl group, an aryl group or a heteroaryl group, or $R^{71}$ and $R^{72}$ together form an alkylene group having 2 to 5 carbon atoms, m is 0, 1 or 2, Q is a group of the formula $COOR^8$ (wherein $R^8$ is a hydrogen atom or a lower alkyl group), a sulfo group or a 1H-tetrazol-5-yl group, each of $R^{91}$ and $R^{92}$ is independently a hydrogen atom, or a lower alkyl group or a lower alkenyl group which may have one to three substituents selected from the group consisting of a hydroxyl group, a lower alkoxy group, a mercapto group, a lower alkylthio group, a carboxyl group, a carbamoyl group, an amino group, a guanidino group, an aryl group and a heteroaryl group, or $R^{91}$ and $R^{92}$ together form an alkylene group having from 2 to 4 carbon atoms wherein optional one hydrogen atom in the alkylene group may be replaced by a hydroxyl group, and one sulfur atom may be present, and U and W together form a single bond; or a pharmaceutically acceptable salt thereof.

In addition, the present invention provides a 2-cyanotryptophan or a protected compound thereof of the formula:

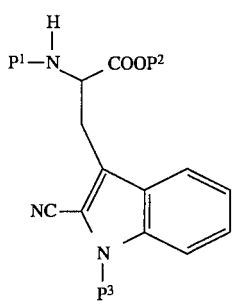

(V)

wherein P¹ is a hydrogen atom or an amino-protecting group, P² is a hydrogen atom or a carboxyl-protecting group, and P³ is a hydrogen atom or an indolyl-protecting group, which is a key intermediate for preparing the above-mentioned peptide derivatives.

Now, the present invention will be described in further detail with reference to the preferred embodiments.

Now, the meanings of various abbreviations used in this specification will be given.

| Abbreviation | Meaning of Abbreviation |
|---|---|
| Ile | L-isoleucine |
| Leu | L-leucine |
| γMeLeu | γ-methyl-L-leucine |
| DNle | D-norleucine |
| DNva | D-norvaline |
| DTrp | D-tryptophan |
| Boc | tert-butoxycarbonyl |
| Me | methyl |
| ᵗBu | tert-butyl |
| Bzl | benzyl |
| Cpeg | L-cyclopentylglycine |
| CDI | 1,1'-carbonyldiimidazole |
| DCC | N,N'-dicyclohexylcarbodiimide |
| DMAP | 4-(dimethylamino)pyridine |
| DMF | N,N-dimethylformamide |
| DMSO | dimethylsulfoxide |
| NMM | N-methylmorpholine |
| EDCI.HCl | 1-ethyl-3-(3-dimethylamino-propyl)carbodiimide.hydrochloride |
| HOBT.H₂O | 1-hydroxy-1H-benzotriazole monohydrate |
| TEA | triethylamine |
| TFA | trifluoro acetic acid |
| THF | tetrahydrofuran |
| TsOH | p-toluene sulfonic acid |
| MOPS | 3-morpholinopropane sulfonic acid |
| HEPES | 2-[4-(2-hydroxyethyl)-1-piperazinyl]ethane sulfonic acid |
| Tris | tris(hydroxymethyl)aminomethane |
| PMSF | phenylmethanesulfonyl=fluoride |
| DAsp | D-aspartic acid |
| DtertLeu | D-2-amino-3,3-dimethylbutanoic acid |
| DPen | D-penicillamine |
| DPen(Me) | S-methyl-D-penicillamine |
| Pip | L-pipecolinic acid |
| Pro | L-proline |
| DTrp(2-Cl) | 2-chloro-D-tryptophan |
| DTrp(2-Br) | 2-bromo-D-tryptophan |
| DTrp(1-Boc, 2-Cl) | 1-tert-butoxycarbonyl-2-chloro-D-tryptophan |
| DTrp(1-Boc, 2-Br) | 1-tert-butoxycarbonyl-2-bromo-D-tryptophan |
| DTrp(1-Boc, 2-CN) | 1-tert-butoxycarbonyl-2-cyano-D-tryptophan |
| DTrp(2-CN) | 2-cyano-D-tryptophan |
| Val | L-valine |
| Fmoc | 9-fluorenylmethoxycarbonyl |
| Pac | phenacyl |
| Pfp | pentafluorophenyl |

| Abbreviation | Meaning of Abbreviation |
|---|---|
| DIPC | N,N'-diisopropylcarbodiimide |
| EDT | 1,2-etanedithiol |
| Pd/C | palladium on activated carbon |

Now, the definitions of the various terms mentioned in this specification will be explained.

In this specification, the lower alkyl group means a straight or branched chain hydrocarbon group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The cycloalkyl group may, for example, be a cyclopropyl, cyclobutyl, cyclopentyl, cyclohexyl, cycloheptyl, cyclooctyl or cyclononyl group.

The cycloalkyl lower alkyl group means an alkyl group having 1 to 6 carbon atoms which is substituted with a cycloalkyl group having 3 to 6 carbon atoms such as a cyclopropylmethyl, 1-cyclopropylethyl, 2-cyclopropylethyl, 1-cyclopropylpropyl, 2-cyclopropylpropyl, 3-cyclopropylpropyl, cyclopentylmethyl, 2-cyclopentylethyl, cyclohexylmethyl, 2-cyclohexylethyl, 2-cyclohexylpropyl group.

The aryl group may, for example, be a phenyl, 1-naphthyl or 2-naphthyl group.

The aryl lower alkyl group means a lower alkyl group which is substituted with an aryl group defined above such as a benzyl, 2-phenylethyl, 3-phenylpropyl, 5-phenylpentyl, 6-phenylhexyl, 1-phenylethyl, 1-naphthylmethyl, 2-(1-naphthyl)ethyl, 3-(1-naphthyl)propyl group.

The heteroaryl group means a heterocyclic or fused heterocyclic group containing at least one hetero atom such as an oxygen, nitrogen or sulfur atom, for example, a thienyl, furyl, thiazolyl, imidazolyl, pyridyl, indolyl or benzothienyl group.

The heteroaryl lower alkyl group means a lower alkyl group which is substituted with a heteroaryl group defined above such as a 2-thienylmethyl, 2-(2-thienyl)ethyl, 3-(2-thienyl)propyl, 2-furylmethyl, 2-(2-furyl)ethyl, 2-thiazolylmethyl, 4-imidazolylmethyl, 2-(4-imidazolyl)ethyl, 3-(4-imidazolyl)propyl, 2-pyridylmethyl, 2-(2-pyridyl)ethyl, 3-indolylmethyl, 3-benzothienylmethyl group.

The lower alkenyl group means a straight or branched chain hydrocarbon group of 2 to 6 carbon atoms having at least one double bond such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The alkylene group means a straight chain bridge of 1 to 6 carbon atoms connected by single bonds such as a methylene, ethylene or propylene group.

The lower alkoxy group means a straight or branched chain alkoxy group having 1 to 6 carbon atoms such as a methoxy, ethoxy, propoxy or isopropoxy group.

The halogen atom means a fluorine, chlorine, bromine or iodine atom.

The lower alkylthio group means a straight or branched chain alkylthio group having 1 to 6 carbon atoms such as a methylthio, ethylthio, propylthio, isopropylthio group.

The acyl group means a group derived from organic acids by deletion of an OH group such as a formyl, acetyl, propionyl, benzoyl, methoxycarbonyl, ethoxycarbonyl, propoxycarbonyl, phenoxycarbonyl, N-methylcarbamoyl, N-ethylcarbamoyl, N,N-dimethylcarbamoyl, methylsulfonyl, ethylsulfonyl, phenylsulfonyl, dimethylphosphoryl or diethylphosphoryl group.

The amino-protecting group means a urethane type protecting group such as a t-butoxycarbonyl, benzyloxycarbonyl, p-methoxybenzyloxycarbonyl or 9-fluorenylmethoxycarbonyl group, an acyl type protecting group such as a formyl, trifluoroacetyl or tosyl group, or an alkyl type protecting group such as a trityl group.

The carboxyl-protecting group means a group which forms an ester such as a methyl, ethyl, t-butyl, benzyl or phenacyl ester.

The indolyl-protecting group may, for example, be a formyl, t-butoxycarbonyl, benzyloxycarbonyl or benzenesulfonyl group.

Now, this invention will be described in more detail with reference to specific examples for the various symbols used in the formula (I) and (V).

$R^2$ means a hydrogen atom or a lower alkyl group. Examples of the lower alkyl group are methyl and ethyl groups.

$R^3$ means a lower alkyl group which is unsubstituted or substituted with a lower alkylthio group, a lower alkenyl group, a cycloalkyl group or a cycloalkyl lower alkyl group wherein optional one to four hydrogen atoms on the ring may independently be replaced by a lower alkyl group, an aryl group, a heteroaryl group, an aryl lower alkyl group or a heteroaryl lower alkyl group. Examples of the lower alkyl group which is unsubstituted or substituted with a lower alkylthio group are methyl, ethyl, methylthioethyl, propyl, isopropyl, butyl, isobutyl, sec-butyl, tert-butyl, pentyl, isopentyl, neopentyl and tert-pentyl groups. Examples of the lower alkenyl group are vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl and 4-pentenyl groups. Examples of the cycloalkyl group or the cycloalkyl lower alkyl group wherein optional one to four hydrogen atoms on the ring may independently be replaced by a lower alkyl group are cyclopropyl, 2-methylcyclopropyl, 2-ethylcyclopropyl, 2-propylcyclopropyl, 2,2-dimethylcyclopropyl, 2,3-dimethylcyclopropyl, 2,2,3,3-tetramethylcyclopropyl, cyclobutyl, cyclopentyl, cyclohexyl, cyclopropylmethyl, 2-methylcyclopropylmethyl, 2-ethylcyclopropylmethyl, 2-propylcyclopropylmethyl, 2,2-dimethylcyclopropylmethyl, 2,3-dimethylcyclopropylmethyl, 2,2,3,3-tetramethylcyclopropylmethyl, cyclobutylmethyl, cyclopentylmethyl, cyclohexylmethyl, 1-cyclopropylethyl, 2-cyclopropylethyl, 1-cyclopropyl-1-methylethyl, 1-cyclobutylethyl, 2-cyclobutylethyl, 1-cyclobutyl-1-methylethyl, 1-cyclopentylethyl, 2-cyclopentylethyl, 1-cyclopentyl-1-methylethyl, 1-cyclohexylethyl, 1-cyclohexyl-1-methylethyl, 1-cycloheptylethyl and 1-cyclooctylethyl groups. Examples of the aryl group are phenyl and 1-naphthyl groups. Examples of the heteroaryl group are 2-thienyl, 2-thiazolyl and 2-furyl groups. Examples of the aryl lower alkyl group are benzyl and 2-phenylethyl groups. Examples of the heteroaryl lower alkyl group are 2-thienylmethyl, 2-(2-thienyl)ethyl, 2-thiazolylmethyl, 2-furylmethyl, 2-pyridylmethyl, 3-indolylmehtyl and 3-benzothienylmethyl groups.

$R^4$ means a hydrogen atom, a lower alkyl group or an acyl group. Examples of the lower alkyl group are methyl and ethyl groups. Examples of the acyl group are formyl, acetyl, propionyl, benzoyl, methoxycarbonyl, ethoxycarbonyl, propoxycarbonyl, phenoxycarbonyl, N-methylcarbamoyl, N-ethylcarbamoyl, N,N-dimethylcarbamoyl, methylsulfonyl, ethylsulfonyl, phenylsulfonyl, dimethylphosphoryl and diethylphosphoryl groups.

In X, $R^{11}$ means a lower alkyl group or an aryl group. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl and 1,1,2-trimethylpropyl groups. Examples of the aryl group are phenyl, 1-naphthyl and 2-naphthyl groups.

In X, $R^{12}$ means a lower alkyl group, a cycloalkyl group, a cycloalkyl lower alkyl group, a 1-adamantyl group, an aryl group or a heteroaryl group wherein 1 or 2 optional hydrogen atoms on the ring may be replaced by an optional group selected from the group consisting of a lower alkyl group, a lower alkoxy group, a halogen atom, a trifluoromethyl group, a nitro group, an amino group and a formylamino group. Otherwise, $R^{12}$ and $R^{13}$ may form, together with the adjacent nitrogen atom, a heterocyclic group as indicated below. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl and 1,1,2-trimethylpropyl groups. Examples of the cycloalkyl group are cyclopropyl, cyclobutyl, cyclopentyl, cyclohexyl and cycloheptyl groups. Examples of the cycloalkyl lower alkyl group are cyclopropylmethyl, 1-cyclopropylethyl, 2-cyclopropylethyl, 1-cyclopropylpropyl, 2-cyclopropylpropyl, 3-cyclopropylpropyl, cyclopentylmethyl, 2-cyclopentylethyl, cyclohexylmethyl, 2-cyclohexylethyl, 3-cyclohexylpropyl groups. Examples of the aryl group or a heteroaryl group wherein 1 or 2 optional hydrogen atoms on the ring may be replaced by an optional group selected from the group consisting of a lower alkyl group, a lower alkoxy group, a halogen atom, a trifluoromethyl group, a nitro group, an amino group and a formylamino group, are phenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2,6-difluorophenyl, 2,6-dichlorophenyl, 2,6-dibromophenyl, 2-aminophenyl, 2-formylaminophenyl, 2-trifluoromethylphenyl, 2-nitrophenyl, 3-aminophenyl, 3-formylaminophenyl, 2-pyridyl, 3-pyridyl, 4-pyridyl, 2-thienyl and 3-thienyl groups.

In X, $R^{13}$ means a hydrogen atom, a lower alkyl group which is unsubstituted or substituted with a hydroxyl group, a cycloalkyl group or a cycloaokyl lower alkyl group. Otherwise, $R^{13}$ and $R^{12}$ may form, together with the adjacent nitrogen atom, a heterocyclic group as indicated below. Examples of the lower alkyl group which is unsubstituted or substituted with a hydroxyl group are methyl, ethyl, propyl, isopropyl, butyl, isobutyl, sec-butyl, tert-butyl, pentyl, isopentyl, neopentyl, tert-pentyl, hydroxymethyl, 2-hydroxyethyl and 3-hydroxy propyl groups. Examples of the cycloalkyl group are cyclopropyl, cyclobutyl, cyclopentyl, cyclohexyl and cycloheptyl groups. Examples of the cycloalkyl lower alkyl group are cyclopropylmethyl, 1-cyclopropylethyl, 2-cyclopropylethyl, 1-cyclopropylpropyl, 2-cyclopropylpropyl, 3-cyclopropylpropyl, cyclopentylmethyl, 2-cyclopentylethyl, cyclohexylmethyl, 2-cyclohexylethyl, 3-cyclohexylpropyl groups.

In X, $R^{12}$ and $R^{13}$ may also form, together with the adjacent nitrogen atom, a 5- to 9-membered nitrogen-containing saturated heterocyclic group having 4 to 8 carbon atoms. Among methylene groups forming the heterocycle, one optional methylene group not adjacent to the above nitrogen atom may be replaced by a thio group, and one to four optional hydrogen atoms on the carbon atoms of the heterocycle may independently be replaced by a lower alkyl group or a hydroxy lower alkyl group, and further two adjacent carbon atoms in the heterocycle may form a fused-benzene ring. Examples of the heterocyclic group are pyrrolidino, piperidino, perhydroazepin-1-yl, perhydroazocin-1-yl, perhydroazonin- 1-yl, 1,3-thiazolidin-1-yl, indolin-1-yl, isoindolin-2-yl, 3-pyrolin-1-yl, 1,5-dihydro-2H-pyrrol-1-yl, perhydro-1,4-thiadin-4-yl, 1,2,3,4-tetrahydroquinolin-1-yl, 1,2,3,4-tetrahydroisoquinolin-2-yl, 1,2,3,4-tetrahydropyridin-1-yl, 1,2,3,6-tetrahydropyridin- 1-yl, perhydro-1,4-thiazepin-4-yl, 2,3,4,5-tetrahydro- 1-benzazepin-1-yl, 2,3,4,5-tetrahydro-2-benzazepin- 2-yl, 1,2,4,5-tetrahydro-3-benzazepin-3-yl, 2,3,4,5-tetrahydro-lH-azepin-1-yl, 2,3,6,7-tetrahydro- 1H-azepin-1-yl, 1,3,4,7-tetrahydro-2H-azepin-1-yl, perhydro- 1,4-thiazocin-4-yl, 1,2,3,4,5,6-hexahydro-1-benzazocin- 1-yl, 1,2,3,4,5,6-hexahydro-2-benzazocin- 2-yl, 1,2,3,4,5,6-hexahydro-3-benzazocin-3-yl, 1,2,3,4,5,6-hexahydroazocin-1-yl, 1,2,3,4,7,8-hexahydroazocin- 1-yl and 1,2,3,4,5,8-hexahydroazocin-1-yl groups, or the above-mentioned heterocyclic groups wherein one to four optional hydrogen atoms on the carbon atoms of the heterocycle may independently be replaced by a lower alkyl group or a hydroxy lower alkyl group. Examples of the lower alkyl group are methyl, ethyl, propyl, isopropyl, butyl, isobutyl, sec-butyl and tert-butyl groups. Examples of the hydroxy lower alkyl group are hydroxymethyl, 2-hydroxyethyl, 2-hydroxypropyl, 3-hydroxypropyl, 2-hydroxybutyl, 3-hydroxybutyl and 4-hydroxybutyl groups.

In Y, $R^5$ means a hydrogen atom, or a lower alkyl or lower alkenyl group which may have 1 to 3 substituents selected from the group consisting of hydroxyl, lower alkoxy, lower alkylthio, aryl and heteroaryl groups. Examples of the lower alkyl or lower alkenyl group which may be substituted by 1 to 3 substituents selected from the group consisting of hydroxyl, lower alkoxy, lower alkylthio, aryl and heteroaryl groups, are methyl, ethyl, propyl, isopropyl, butyl, isobutyl, sec-butyl, tert-butyl, pentyl, isopentyl, neopentyl, tert-pentyl, hexyl, hydroxymethyl, 1-hydroxyethyl, methoxymethyl, 1-methoxyethyl, methylthiomethyl, ethylthiomethyl, propylthiomethyl, butylthiomethyl, 2-methylthioethyl, 2-ethylthioethyl, 3-indolylmethyl, 4-imidazolylmethyl, vinyl, allyl, 2-propenyl, isopropenyl, 3-butenyl, 2-butenyl, 1-butenyl, 1-methyl-2-propenyl, 1-methyl- 1-propenyl, 1-ethyl-1-ethenyl, 2-methyl-2-propenyl, 2-methyl-1-propenyl, 4-pentenyl, 1-hydroxy-2-propenyl, 1-methoxy-2-propenyl, 1-methylthio-2-propenyl, 2-hydroxy-3-butenyl and 2-ethylthio-3-butenyl groups.

In Y, Z means a hydroxymethyl group, a group of the formula $CO_2R^{61}$, a group of the formula $CONR^{62}R^{63}$, a 1H-tetrazole-5-yl group, a sulfo group or a phosphono group.

In Z, $R^{61}$ means a hydrogen atom or a lower alkyl group. Examples of the lower alkyl group are methyl, ethyl, propyl, isopropyl, butyl, isobutyl, sec-butyl, tert-butyl, pentyl, isopentyl, neopentyl and hexyl groups.

In Z, each of $R^{62}$ and $R^{63}$ means independently a hydrogen atom, an aryl group, a heteroaryl group or a lower alkyl group which may have 1 to 3 substituents selected from the group consisting of a hydroxyl group, a carboxyl group and a sulfo group. Examples of the aryl group are phenyl 1-naphthyl and 2-naphthyl groups. Examples of the heteroaryl group are 2-thienyl, 3-thienyl, 2-furyl and 3-furyl groups. Examples of the lower alkyl group which may have 1 to 3 substituents selected from the group consisting of a hydroxyl group, a carboxyl group and a sulfo group, are methyl, ethyl, propyl, 2-hydroxyethyl, carboxymethyl, 1-carboxyethyl, 2-carboxyethyl, sulfomethyl and 2-sulfoethyl groups.

In X, $R^{71}$ means a hydrogen atom. Otherwise, $R^{71}$ and $R^{72}$ may form an alkylene group having 2 to 5 carbon atoms.

In X, $R^{72}$ means a lower alkyl group which is unsubstituted or substituted with a lower alkylthio group, a cycloalkyl group, an aryl group or a heteroaryl group. Otherwise, $R^{72}$ and $R^{71}$ may form an alkylene group having 2 to 5 carbon atoms. Example of the lower alkyl group which is unsubstituted or substituted with a lower alkylthio group are methyl, ethyl, propyl, isopropyl, butyl, isobutyl, sec-butyl, tert-butyl, pentyl, isopentyl, neopentyl, hexyl, methylthiomethyl, 1-methylthioethyl, 2-methylthioethyl, 1-methyl-1-methylthioethyl, 1-methyl-1-methylthiopropyl, 1-methyl-1-ethylthioethyl and 1-methyl-1-propylthioethyl groups.

In X, $R^{71}$ and $R^{72}$ may also form an alkylene group having 2 to 5 carbon atoms. Example of the alkylene group having 2 to 5 carbon atoms are groups of the formula $—(CH_2)_2—$, $—(CH_2)_3—$, $—(CH_2)_4—$, $—(CH_2)_5—$.

In X and Y, U and W form, together with each other, a single bond.

In Y, m means 0, 1 or 2.

In Y, Q means a group of the formula $COOR^8$, a sulfo group or a 1H-tetrazol-5-yl group. In Q, $R^8$ means a hydrogen atom or a lower alkyl group. Examples of the lower alkyl group are methyl, ethyl, propyl, isopropyl, butyl, isobutyl, sec-butyl, tert-butyl, pentyl, isopentyl, neopentyl and hexyl groups.

In Y, each of $R^{91}$ and $R^{92}$ means independently a hydrogen atom, a lower alkyl group or a lower alkenyl group which may have 1 to 3 substituents selected from the group consisting of a hydroxy group, a lower alkoxy group, a mercapto group, a lower alkylthio group, a carboxyl group, a carbamoyl group, an amino group, a guanidino group, an aryl group and a heteroaryl group. Otherwise, $R^{91}$ and $R^{92}$ may form, together with each other, an alkylene group having 2 to 4 carbon atoms wherein optional one hydrogen atom in the alkylene group may be replaced by a hydroxyl group, and further one sulfur atom may be present. Examples of the lower alkyl group or the lower alkenyl group which may have 1 to 3 substituents selected from the group consisting of a hydroxyl group, a lower alkoxy group, a mercapto group, a lower alkylthio group, a carboxyl group, a carbamoyl group, an amino group, a guanidino group, an aryl group and a heteroaryl group, are hydroxymethyl, mercaptomethyl, carbamoylmethyl, 2-carbamoylethyl, carboxymethyl, 2-carboxyethyl, 4-aminobutyl, 3-guanidinopropyl, 4-imidazolylmethyl, 3-indolylmethyl, phenylmethyl and (4-hydroxyphenyl)methyl groups. Examples of the alkylene group having 2 to 4 carbon atoms wherein optional one hydrogen atom in the alkylene group may be replaced by a hydroxyl group, and further one sulfur atom may be present, are groups of the formula $—(CH_2)_2—$, $—(CH_2)_3—$, $—(CH_2)_4—$, $—CH_2—S—CH_2—$ and $—CH_2—CH(OH)—CH_2—$.

$P^1$ means a hydrogen atom or an amino-protecting group. Examples of the amino-protecting group are t-butoxycarbonyl, benzyloxycarbonyl, p-methoxybenzyloxycarbonyl, 9-fluorenylmethoxycarbonyl, formyl, trifluoroacetyl, tosyl and trityl groups.

$P^2$ means a hydrogen atom or a carboxyl-protecting group. Examples of the carboxyl-protecting group are groups which form methyl, ethyl, t-butyl, benzyl and phenacyl esters.

$P^3$ means a hydrogen atom or an indolyl-protecting group. Examples of the indolyl-protecting group are formyl, t-butoxycarbonyl, benzyloxycarbonyl and benzenesulfonyl groups.

Now, the process for producing the novel peptide derivatives, and 2-cyanotryptophan and a protected compound thereof of the present invention will be described.

A 2-cyanotryptophan or a protected compound thereof of formula (V) of the present invention may be produced by reacting a compound of formula (VI):

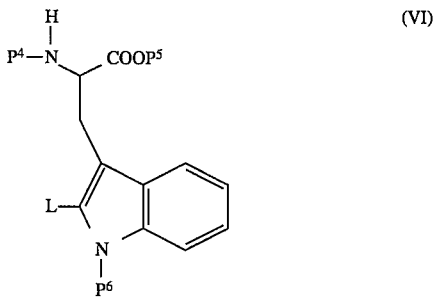

wherein $P^4$ is an amino-protecting group, $P^5$ is a carboxyl-protecting group, $P^6$ is an indolyl-protecting group, and L is a leaving group, with a cyanide such as copper(I) cyanide, sodium cyanide or potassium cyanide in the presence of, if necessary, copper salt such as copper(I) iodide or copper in an inert solvent such as N,N-dimethylformamide, dimethylsulfoxide or pyridine at room temperature to the boiling point of the solvent, preferably at 50° C. to 120° C., for 10 min to 24 h, preferably for 30 min to 8 h, followed by, if necessary, deprotection of the protecting group(s) and protection of functional group(s). Racemization of the α-position of the tryptophan derivative can be avoided during the reaction of the compound of formula (VI) with a cyanide, the deprotection and the protection procedures. Therefore, each D-form, DL-form or L-form of the compound of formula (V) is obtained from each D-form, DL-form or L-form of the compound of formula (VI), respectively.

Examples of the amino-protecting group described by $P^4$ are t-butoxycarbonyl, benzyloxycarbonyl, p-methoxybenzyloxycarbonyl, 9-fluorenylmethoxycarbonyl, formyl, trifluoroacetyl, tosyl and trityl groups.

Examples of the carboxyl-protecting group described by $P^5$ are groups which form methyl, ethyl, t-butyl, benzyl and phenacyl esters.

Examples of the indolyl-protecting group described by $P^6$ are t-butoxycarbonyl, benzyloxycarbonyl and benzenesulfonyl groups.

Examples of the leaving group described by L are chlorine, bromine and iodine atoms, and methanesulfonyl, trifluoromethanesulfonyl and toluenesulfonyl groups.

A peptide derivative of formula (I) of the present invention can be prepared using a 2-cyanotryptophan or a protected compound thereof of formula (V) as a starting material by a method wherein amino acids composing the target peptide derivative are condensed one by one, by a method wherein condensation products of plural amino acids are condensed with each other, or by a combination of such methods, and further, if a peptide derivative of formula (I) is a cyclic pentapeptide, by cyclizing the corresponding linear pentapeptide wherein the side-chain functional groups of the amino acid residues may be protected as the case requires, and then, if necessary, removing a C-terminal protective group or side-chain protective groups.

Condensation can be conducted in a liquid phase or in a solid phase according to known methods such as a DCC method, an azide method, an active ester method and a mixed acid anhydride method (described, for example, by M. Bodansky and M. A. Ondetti in Peptide Synthesis, Interscience, New York, 1966; by F. M. Finn and K. Hofmann in The Proteins, Vol. 2, ed. by H. Nenrath and R. L. Hill, Academic Press Inc., New York, 1976; by Nobuo Izumiya et al. in Peptide Synthesis, Maruzen, 1975).

As a starting material of the peptide derivative of the present invention, both D- and DL-form of a 2-cyanotryptophan or a protected compound thereof can be used, however, the D-form is preferable.

Following methods 1 and 2 will describe the process for producing the novel peptide derivatives of the present invention in more detail.

METHOD 1

Method 1 is a process for producing a peptide derivative of the formula (I), wherein X is a group of the formula $R^{11}$—O—C(=O) or a group of the formula $R^{12}R^{13}N$—C(=O), and Y is a group of the formula (II).

A carboxyl-protecting group of a protected derivative of 2-cyano-D-tryptophan of the formula:

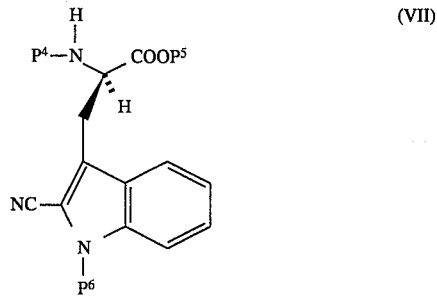

wherein $P^4$, $P^5$ and $P^6$ are as defined above, is deprotected to afford a compound of the formula:

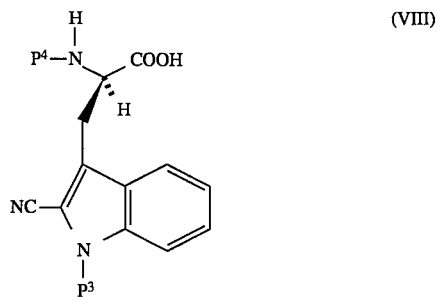

wherein $P^4$ and $P^3$ are as defined above. An amino-protecting group and a carboxyl-protecting group should be selected so that each protecting group can be selectively deprotected. An indolyl-protecting group may be, however, deprotected under the conditions for removing the amino-protecting group or the carboxyl-protecting group. For example, in the case that a Boc group is used for the protection of an amino group, the carboxylic group may be protected as a lower alkyl ester such as a methyl and a ethyl ester, and the indolyl group may be protected by a Boc group. The lower alkyl ester as the carboxyl-protecting group will be readily hydrolysed under alkaline conditions, while the Boc group of the amino-protecting group will be intact under the conditions. On the other hand, the Boc group of the indolyl-protecting group will be deprotected or intact according to the alkaline hydrolysis conditions. Namely, if one equivalent of alkaline is employed under ice-cooling, the Boc group will be intact. On the other hand, if excess of alkaline is employed at room temperature, the Boc group will be deprotected together with the carboxyl-protecting group.

The compound of the formula (VIII) is condensed with a compound of the formula:

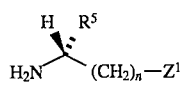

(IX)

wherein $R^5$ and n are as defined above, and $Z^1$ is as defined above or a group of the formula COOP7, wherein P7 is a carboxyl-protecting group, to afford a dipeptide derivative of the formula:

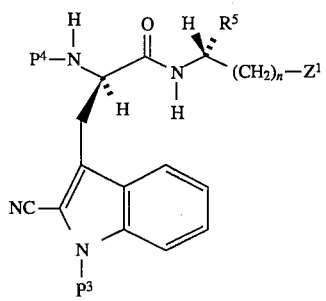

(X)

wherein $P^4$, $P^3$, $R^5$, n and $Z^1$ are defined above.

An N-terminal amino-protecting group of the dipeptide derivative (X) prepared above is now removed, and the resulting deprotected dipeptide is condensed with an amino acid derivative of the formula:

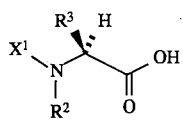

(XI)

wherein $R^2$ and $R^3$ are defined above, and $X^1$ is a group of the formula $R^{11}$—O—C(=O) or a group of the formula $R^{12}R^{13}N$—C(=O) wherein $R^{11}$, $R^{12}$ and $R^{13}$ are defined above, to afforded a tripeptide derivative of the formula:

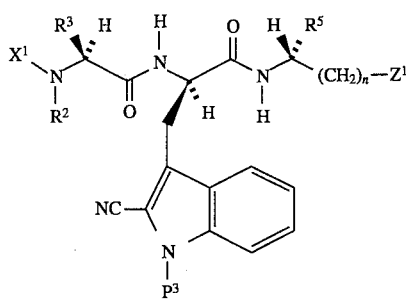

(XII)

wherein $X^1$, $R^2$, $R^3$, $R^5$, $P^3$ and $Z^1$ are defined above.

A C-terminal and/or a side-chain protecting group(s) of the tripeptide derivative prepared above can, if necessary, be deprotected by a suitable method, and further, the peptide derivative can, if necessary, be converted to a pharmaceutically acceptable salt to produce the desired peptide derivative of the formula (I).

In the process so far described, an N-terminal amino acid derivative is lastly condensed to afford the target peptide derivative. The alternative process wherein a C-terminal amino acid derivative is lastly condensed to afford the target product is also available.

Namely, An amino-protecting group of a protected derivative of 2-cyano-D-tryptophan of the formula (VII) is deprotected to afford a compound of the formula:

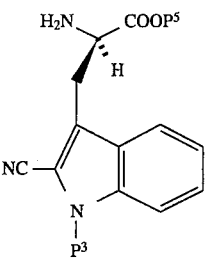

(XIII)

wherein $P^5$ and $P^3$ are as defined above. An amino-protecting group and a carboxyl-protecting group should be selected so that each protecting group can be selectively deprotected. An indolyl-protecting group may be, however, deprotected under the conditions for removing the amino-protecting group or the carboxyl-protecting group. For example, in the case that a Boc group is used for the protection of an amino group, the carboxylic group may be protected as a lower alkyl ester such as a methyl and a ethyl ester, and the indolyl group may be protected by a Boc group. The Boc group of the amino-protecting group will be readily removed by use of a mild acid such as formic acid and TFA, while the lower alkyl ester as the carboxylic acid protection will be intact under the conditions. On the other hand, the Boc group of the indolyl-protecting group will be deprotected together with the amino-protecting group under the conditions.

The compound of the formula (XIII) is condensed with a compound of the formula (XI) to afford a dipeptide derivative of the formula:

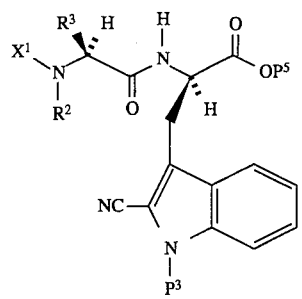

(XIV)

wherein $X^1$, $R^2$, $R^3$, $P^3$ and $P^5$ are defined above.

An carboxyl-protecting group of the dipeptide derivative (XIV) prepared above is now deprotected, and the resulting deprotected dipeptide is condensed with an amino acid derivative of the formula (IX) to afford a tripeptide derivative of the formula (XII).

A C-terminal and/or a side-chain protecting group(s) of the tripeptide derivative prepared above can, if o necessary, be deprotected by a suitable method, and further, the peptide derivative can, if necessary, be converted to a pharmaceutically acceptable salt to produce the desired peptide derivative of the formula (I).

A C-terminal amide peptide derivative of the formula (I) can be prepared by condensation of a compound of the formula:

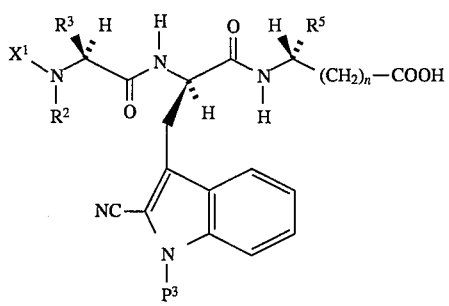

(XV)

wherein $X^1$, $R^2$, $R^3$, $R^5$, n and $P^3$ are defined above, with an amine of the formula:

(XVI)

wherein $R^{62}$ and $R^{63}$ are defined above, by a suitable method such as a DCC method and an active ester method, followed by, if necessary, deprotection of a side-chain protecting group, and further, if necessary, conversion to a pharmaceutically acceptable salt to produce the desired peptide derivative.

METHOD 2

Method 2 is a process for producing a cyclic pentapeptide derivative of the formula (I), wherein X is a group of the formula (III) and Y is a group of the formula (IV).

The cyclic pentapeptide of the present invention is prepared by cyclizing the corresponding linear pentapeptide wherein the side-chain functional groups of the amino acids may be protected as the case requires, and then, if necessary, removal of the side-chain protective groups, and further converting the product to a pharmaceutically acceptable salt, if necessary.

The linear pentapeptide can be prepared by a method wherein an amino acid is condensed one by one, by a method wherein condensation products of plural amino acids are condensed with each other, or by a combination of such methods. Such condensation can be conducted in a liquid phase or in a solid phase.

The preparation of the compound of the present invention by a solid phase method can be conducted in the following manner. The linear pentapeptide can be obtained by successive condensations on an insoluble carrier such as a chloromethyl resin (Biochemistry, 3, 1385 (1964)), an oxymethyl resin (Chem. Ind. (London), 1966, 1597), a p-alkoxybenzyl alcohol resin (J. Am. Chem. Soc., 95, 1328 (1973)) or a functionalized polyamide resin (Bioorganic Chemistry, 8, 351–370 (1979)). Firstly an α-amino group of the amino group o of the amino acid selected for the C-terminus in the linear pentapeptide, is protected. If a reactive functional group is present in the side-chain, such a side-chain functional group is also protected. Then, it is bonded as a carboxylic acid ester to the insoluble carrier in accordance with a known method. Then, the α-amino protective group is removed, and then the next amino acid derivative (the α-amino group and, if necessary, the side-chain functional group are protected) is condensed by simultaneously adding a condensing reagent such as DCC or DIPC, if necessary together with an additive such as HOBT·H$_2$O. This amino acid derivative may be used as a carboxyl-activated amino acid such as a pentafluorophenyl ester or an acid azide. Such deprotection and condensation are repeated to afford a desired linear pentapeptide. The protective group of an amino group is selected usually from those well known in the art, for example from urethane type protective groups such as a Z group, a Boc group, a Fmoc group, a p-methoxybenzyloxycarbonyl group and a p-nitrobenzyloxycarbonyl group. For the protection of an α-amino group, it is preferred to use a Fmoc group or a Boc group. The Fmoc group can be readily deprotected after the condensation with relatively mild base such as a 20% solution of piperidine in DMF. On the other hand, the Boc group can be readily deprotected with relatively mild acid such as TFA. When the Fmoc group is used for the protection of an α-amino group, the side-chain carboxyl group of e.g. aspartic acid or glutamic acid may be protected as a tert-butyl ester or a trityl ester, the hydroxyl group of e.g. tyrosine, serine or threonine may be protected as a tert-butyl ether, the side-chain amino group of e.g. lysine or ornithine and the imidazolyl group of histidine may be protected by a Boc group, the mercapto group of cysteine may be protected by a trityl group, and the guanidino group of arginine may be protected by a pentamethylchromansulfonyl group, so that these protective groups are stable under the conditions for the removal of the Fmoc group, and after the cyclization of the linear pentapeptide, all such protective groups can be simultaneously deprotected with mild acid such as TFA. On the other hand, when the Boc group is used for the protection of the α-amino group, the side-chain carboxyl group of e.g. aspartic acid or glutamic acid may be protected as a benzyl ester, the hydroxyl group of e.g. tyrosine, serine or threonine may be protected as a benzyl ether, and the side-chain amino group of e.g. lysine or ornithine and the imidazolyl group of histidine may be protected by a Z group, so that these protective groups are stable under the conditions for removing the Boc group, and after the cyclization of the linear pentapeptide, all such protective groups can be simultaneously removed by, for example, catalytic hydrogenation, treatment with hydrogen fluoride or treatment with trimethylsilyl trifluoromethanesulfonatethioanisole-TFA (Chem. Pharm. Bull., 35, 3447–52 (1987)).

Cleavage of the linear pentapeptide from the resin after the removal of the N-terminal protective group, can be conducted by various methods well known to those skilled in the art. For example, cleavage of the peptide from the resin with hydrazine affords the corresponding hydrazide. The hydrazide can be cyclized via an azide to afford the desired cyclic pentapeptide. The hydrazide is converted to the corresponding azide by treatment with a reagent which supplies nitrous acid in site. As a reagent suitable for this purpose, there may be mentioned a lower alkyl ester of nitrous acid (such as tert-butyl nitrite or isoamyl nitrite) or an alkali metal salt of nitrous acid (such as sodium nitrite or potassium nitrite) in the presence of strong acid such as hydrochloric acid or sulfuric acid. This reaction can be conducted at ca. −40° C. to 20° C. in water and/or non-aqueous solvent such as DMF, THF or 1,4-dioxane. On the other hand, when a solid phase synthesis is conducted by use of a p-alkoxybenzyl alcohol resin as an insoluble carrier, it is possible to obtain a linear peptide having a carboxyl group as the C-terminus (the side-chain functional groups may be protected as the case requires) by cleavage the peptide with mild acid such as TFA. Such a linear pentapeptide can be cyclized into a cyclic pentapeptide by treatment with a condensing reagent such as DCC (or EDCI·HCl)-HOBT·H$_2$O or diphenylphosphoryl azide in DMF, THF, 1,4-dioxane, acetonitrile, dichloromethane or chloroform at ca. −40 ° C. to 20° C. Such cyclization is conducted preferably under high dilution conditions since the intermolecular reaction is likely to take place in competition with the intramolecular reaction. When the cyclic pentapeptide thus obtained has protective groups in its side-chains, the protective groups can be removed by suitable methods. The cyclic pentapeptide thus obtained may be led to a salt of alkali metal or alkaline earth metal such as sodium, potassium or calcium, an addition salt with basic amino acid such as lysine or arginine, an acid addition salt with mineral acid such as hydrochloric acid or sulfuric acid, an acid addition salt with acidic amino acid such as aspartic acid or glutamic acid, or an acid addition salt with organic acid such as maleic acid, fumaric acid, tartaric acid, malic acid or citric acid.

On the other hand, the linear pentapeptide may be also prepared in a liquid phase by known methods wherein an amino acid is condensed one by one, by a method wherein condensation products of plural amino acids are condensed with each other, or by a combination of such methods.

The protective groups for the N-terminal α-amino group, the C-terminal α-carboxyl group and the reactive functional groups of the side-chains of the linear pentapeptide should be selected according to the cyclization method of the linear pentapeptide.

For example, in the case of an azide method wherein the linear pentapeptide is led to a hydrazide and then cyclized via an azide, it is preferred to protect the N-terminal α-amino group with a Z group, the C-terminal α-carboxyl group as an ester such as a methyl ester, an ethyl ester or a benzyl ester and the side-chain reactive functional groups such as the carboxyl group of e.g. aspartic acid or glutamic acid as a tert-butyl ester or a trityl ester, the hydroxyl group of e.g. tyrosine, serine or threonine as a tert-butyl ether, the amino group of e.g. lysine or ornithine with a Boc group, the imidazolyl group of histidine or the mercapto group of cysteine with a trityl group, and the guanidino group of arginine with a pentamethylchromansulfonyl group. Namely, the full-protected linear pentapeptide obtained after the peptide-condensation is allowed to react with hydrazine to afford the corresponding hydrazide, whose N-terminal Z group is successively removed by catalytic hydrogenation. Under these reaction conditions are intact the protective groups of the side-chain functional groups. Then, after the cyclization reaction, all such side-chain protective groups can be deprotected with mild acid such as TFA. In the case where the peptide has no reactive functional groups at its side-chains, it is also possible to select a Boc group as the protective group for the N-terminal α-amino group in the azide method.

The N-terminal deprotected linear pentapeptide hydrazide obtained by the liquid phase method may be subjected to cyclization via an azide in the same manner as the hydrazide obtained by the solid phase method to afford a cyclic pentapeptide.

In the case where after the removal of the protective group for the N-terminal α-amino group and the C-terminal α-carboxyl group, the linear pentapeptide is cyclized by treatment with condensing reagents such as DCC (or EDCI·HCl)-HOBT·H$_2$O or diphenylphosphorylazide, it is preferred to protect the N-terminal α-amino group with a Boc group, the C-terminal α-carboxyl group as a tert-butyl ester or a phenacyl ester, and the side-chain reactive functional groups such as the carboxyl group of e.g. aspartic acid or glutamic acid as a benzyl ester, the hydroxyl group of e.g. tyrosine, serine or threonine as a benzyl ether, and the amino group of e.g. lysine or ornithine, the imidazolyl group of histidine and the indolyl group of tryptophan with a Z group. Namely, in the case where the C-terminus of the protected linear pentapeptide obtained after the condensation is a tert-butyl ester, the Boc group of the N-terminus and the tert-butyl ester of the C-terminus can be simultaneously removed without removing the side-chain protective groups, by use of mild acid such as TFA. In the case where the C-terminus is a phenacyl ester, the Boc group of the N-terminus can be removed by use of mild acid such as TFA and the phenacyl ester of the C-terminus can be removed by use of zinc/acetic acid, without removing the side-chain protective groups. In each case, all such side-chain protective groups can be removed after cyclization by a method such as catalytic hydrogenation. Further, in the case where the N-terminal α-amino group is protected by a Z group and the C-terminal α-carboxyl group is protected as a benzyl ester or a phenacyl ester, the side-chain reactive functional groups may be protected in such manner that the carboxyl group of e.g. aspartic acid or glutamic acid be protected as a tert-butyl ester or a trityl ester, the hydroxyl group of e.g. tyrosine, serine or threonine be protected as a tert-butyl ether, and the amino group of e.g. lysine or ornithine and the imidazolyl group of histidine be protected with a Boc group, so that these side-chain protective groups will not be removed under the conditions for the removal of the protective groups for the N-terminal α-amino group and the C-terminal α-carboxyl group. After the cyclization, all such side-chain protective groups can be removed by use of mild acid such as TFA.

The linear pentapeptide thus obtained can be subjected to cyclization by treatment with condensing reagents in the same manner as the linear pentapeptide obtained by the solid phase method, to afford a cyclic pentapeptide. Otherwise, such a linear pentapeptide may be led to an active ester such as a p-nitrophenyl ester or an N-hydroxysuccinimide ester with the protected N-terminal α-amino group, and then the resulting active ester can be cyclized by the deprotection of the N-terminal α-amino group.

The cyclic pentapeptide thus obtained may be subjected, if necessary, to removal of protective groups, and may be subjected to formation of a salt or exchange of a salt, as the case requires, to afford a desired cyclic pentapeptide of the present invention or a pharmaceutically acceptable salt thereof.

All reaction intermediates and products so far described can be purified by well-known methods such as recrystallization, reprecipitation, partition procedures, normal- or reverse-phase chromatography and ion-exchange chromatography.

Starting materials used in the methods so far described are commercially available except for the following materials, which are prepared by the known method in the literature.

D-cyclopentylglycine: J. Org. Chem., 30, 1320 (1965).

α-N-trifluoroacetyl-2-bromo-D-tryptophan methyl ester: J. Am. Chem. Soc., 108, 2023 (1986).

The chemical structures, Example Nos. and compound Nos. of the prepared peptide derivatives in the present invention are shown in Tables 1 and 2.

TABLE 1

| Exp. No. | Compd. No. | R³ | R⁵ | Z |
|---|---|---|---|---|
| 2 | 1 | $-CH(CH_3)_2$ | $-CH_2CH_2CH_2CH_3$ | $-COOH$ |
| 3 | 2 | $-CH_2CH(CH_3)_2$ | $-CH_2CH_2CH_2CH_3$ | $-COOH$ |
| 4 | 3 | $-CH_2C(CH_3)_3$ | $-CH_2CH_2CH_2CH_3$ | $-COOCH_3$ |
| 4 | 4 | $-CH_2C(CH_3)_3$ | $-CH_2CH_2CH_2CH_3$ | $-COOH$ |
| 5 | 5 | $-CH(CH_3)_2$ | $-CH_2CH_2CH_3$ | $-COOH$ |
| 6 | 6 | $-CH(CH_3)CH_2CH_3$ | $-CH_2CH_2CH_3$ | $-COOH$ |
| 7 | 7 | cyclopentyl | $-CH_2CH_2CH_3$ | $-COOCH_3$ |
| 7 | 8 | cyclopentyl | $-CH_2CH_2CH_3$ | $-COOH$ |
| 8 | 9 | cyclopentyl | $-CH_2CH_2CH_3$ | $-CONHCH_3$ |

TABLE 2

| Exp. No. | Compd. No. | R⁷² | Q |
|---|---|---|---|
| 9 | 10 | $-C(CH_3)_2SCH_3$ | $-COOCH_3$ |
| 9 | 11 | $-C(CH_3)_2SCH_3$ | $-COOH$ |
| 10 | 12 | $-CH(CH_3)_2$ | $-COOH$ |

Now, the endothelin antagonistic properties of the peptide derivatives of the present invention will be described.

ENDOTHELIN BINDING INHIBITION TEST

The cerebellum of porcine was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 3.3 mg/ml. Then, 16 μl of this membrane suspension was added to 340 μl of 50 mM tris/HCl buffer, pH 7.4, containing 10 μl calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding; 0.2 μM as the final concentration), (B) buffer solution A (for total control binding), or (C) a test compound (1.1 μM as the final concentration), was added. Further, to each suspension, 40 μl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM of the test compound was determined by the following equation.

$$D\ (\%) = 100 - \frac{(C) - (A)}{(B) - (A)} \times 100$$

Each test was performed in triplicate.

TABLE 3

| $^{125}$I-endothelin-1 binding inhibition by 1.1 μM of the test compound | |
|---|---|
| Compd. No. | Inhibition (%) |
| 1 | 96 |
| 2 | 99 |
| 3 | 99 |
| 4 | 100 |
| 5 | 93 |
| 6 | 96 |
| 7 | 96 |
| 8 | 96 |
| 9 | 100 |
| 10 | 65 |
| 11 | 97 |
| 12 | 78 |

As shown in Table 3, the compounds of the present invention were found to be very potent inhibitor of endothelin binding to $ET_B$ receptor. The test compounds are indicated by compound Nos.

On the other hand, each of the representative compounds (Reference Compounds 1, 2 and 3) of the endothelin antagonistic peptides described in EP 0460679A2 and each of the representative compounds (Reference compounds 4, 5 and 6) of the endothelin antagonistic cyclic pentapeptides described in EP 0436189A1 showed, at a concentration of 1.1 μM, 69, 77, 86, 85, 85 or 82% of the $^{125}$I-ET-1 binding inhibition to porcine aorta membrane suspension containing a large amount of $ET_A$ receptors, and, on the contrary, only 6.4, 3.8, 10, 10, 0.6 or 11% of the $^{125}$I-ET-1 binding inhibition to $ET_B$ receptors of porcine cerebellum membrane suspension used in the present experiments.

REFERENCE COMPOUND 1

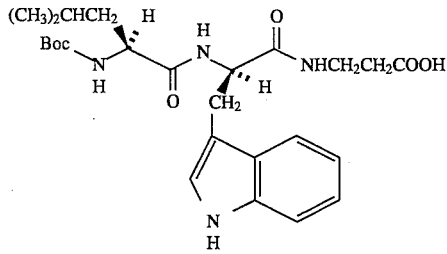

REFERENCE COMPOUND 2

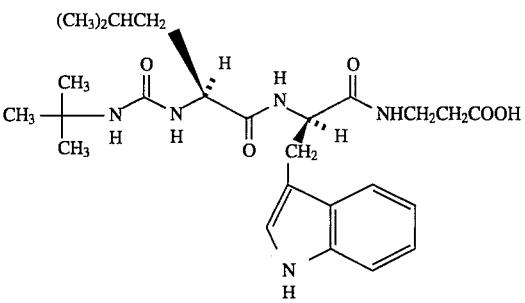

REFERENCE COMPOUND 3

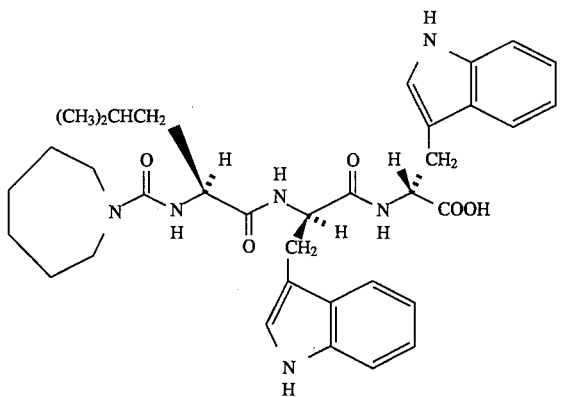

REFERENCE COMPOUND 4 cyclo(-DTrp-DAsp-Pro-DVal-Leu-)

REFERENCE COMPOUND 5 cyclo(-DTrp-DCys(O$_3$Na)-Pro-DVal-Leu-)

REFERENCE COMPOUND 6 cyclo(-DTrp-DAsp-Pro-DThg-Leu-)

Inhibitory activities of test compounds against endothelin-1-induced increase in intracellular calcium concentration of human Girardi heart cells Antagonism of test compounds to endothelin-1-induced increase in intracellular calcium concentration was evaluated in human Girardi heart cells (Dainippon Seiyaku Co., Ltd.).

Cultured human Girardi heart cells in Flask were harvested using 0.25% trypsin and 0.02% EDTA. The collected cells were washed with Dulbecco's modification eagle medium containing 20 mM Hepes and 0.3% BSA (pH 7.4, D medium). Then the cells were suspended in D medium and incubated with 2 μM of fura-2 acetoxymethyl ester at 37° C. for 30 minutes. The cell suspensions were diluted with a 10-fold volume of D medium and incubated for 20 minutes. The fura-2-loaded cells were collected by centrifugation and resuspended in Krebs-Henseleit Hepes buffer (pH 7.4). The resultant suspension in a cuvette was continuously stirred at 37° C. throughout the following measurement process. Each test compound or vehicle was given 5 minutes before the addition of 100 nM ET-1, and fluorescence intensity at emission wavelength of 510 nm and excitation wavelength of 340 and 380 nm was monitored with a JASCO CAF-100 spectrofluorometer (Japan), and [Ca$^{2+}$]i values were calculated according to the reported method (G. Grynkiewicz et al., J. Biol. Chem. 260, 3440–3450 (1985)).

Addition of 1.1 μM of compound No.1 and No.11 to the fura-2-loaded cells inhibited increase in intracellular calcium concentration by 94 and 69%, respectively. Furthermore, compounds No. 1 and No. 11 have no effect on the intracellular calcium concentration itself. These data indicate that the compounds of the present invention show remarkable antagonism against ET-1-induced increase in the intracellular calcium concentration of human Girardi heart cells.

Thus, the compounds of the present invention have excellent endothelin antagonistic activities and are useful as vasodilators for bronchodilators in the field of medicines, and they can be drugs for treating hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, endotoxin shock endotoxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples illustrate the present invention more specifically. It should be understood that the present invention is not limited to these examples alone.

EXAMPLE 1

Synthesis of α-N,1-bis(t-butoxycarbonyl)-2-cyano-D-tryptophan methyl ester (1-a) Preparation of 2-bromo-α-N,1-bis(t-butoxycarbonyl)- D-tryptophan methyl ester To a solution of 2-bromo-α-N-t-butoxycarbonyl-D-tryptophan methyl ester (2.37 g) in acetonitrile (15 mL) were added di-t-butyl dicarbonate (6.60 g) and DMAP (74 mg). The mixture was stirred at room temperature for 4 h then cooled to 0° C. To the mixture was added 3-dimethylaminopropylamine (3.02 mL) and the mixture was allowed to warm to room temperature. After being stirred at room temperature for 5 min, the mixture was concentrated under reduced pressure. The residue was dissolved in ethyl acetate (100 mL), and the solution was washed successively with 10% aq. citric acid (50 mL), sat. aq. NaHCO$_3$ (50 mL) and brine (50 mL), dried over MgSO$_4$ and evaporated to give the product (3.00 g).

m.p.: 58°–62° C.

FAB-MS(m/e, $(C_{22}H_{29}BrN_2O_6)^+$): 496 and 498

$^1$H-NMR(200 MHz,CDCl$_3$, δ ppm): 1.40(9H,s),1.70(9H,s),3.10–3.40(2H,m),3.68(3H,s), 4.52–4.71(1H,m),5.15(1H,d,J=7.7 Hz),7.15–7.40(2H,m), 7.50(1H,d,J=7.3 Hz), 8.05(1H,d,J=7.3 Hz)

Optical Rotations: $[\alpha]_D^{20}$=+5.83° (c 1.0, MeOH)

Analysis for $C_{22}H_{29}BrN_2O_6$: calcd: C 53.13%, H 5.88%, N 5.63% found: C 53.31%, H 5.86%, N 5.56%

(1-b) Preparation of α-N,1-bis(t-butoxycarbonyl)- 2-cyano-D-tryptophan methyl ester To a solution of 2-bromo-α-N,1-bis(t-butoxycarbonyl)-D-tryptophan methyl ester (500 mg, prepared in Example (1-a)) in DMF (1 mL) was added copper(I) cyanide (225 mg), and the mixture was stirred at 85° C. for 1 h. After cooling, the mixture was diluted with ethyl acetate (80 mL), washed with sat. aq. NaHCO$_3$ (50 mL) and brine (50 mL), dried over MgSO$_4$ and evaporated under reduced pressure. The residue was purified by silica gel chromatography (Merck, Kieselgel 60) with ethyl acetate for elution to give the title compound (442 mg) as a colorless amorphous.

High Resolution FAB-MS(m/e, $(C_{23}H_{29}N_3O_6+H)^+$): calcd: 444.2135 found: 444.2136

$^1$H-NMR(300 MHz,CDCl$_3$, δ ppm): 1.41(9H,s),1.71(9H,s),3.34(1H,dd,J=5.9 Hz,14.2 Hz), 3.49(1H,dd,J=5.9 Hz,14.2 Hz),3.79(3H,s),4.67–4.74 (1H,m),5.20(1H,d,J=7.5 Hz), 7.34(1H,t,J=7.8 Hz),7.50 (1H,t,J=7.8 Hz),7.69(1H,d,J=7.8 Hz),8.21(1H,d,J=7.8 Hz)

Optical Rotations: $[\alpha]_D^{20}$=+4.26° (c 1.0 MeOH)

EXAMPLE 2

Synthesis of Compound 1

(2-a) Preparation of α-N-t-butoxycarbonyl-2-cyano-D-tryptophan

To a solution of α-N,1-bis(t-butoxycarbonyl)-2-cyano-D-tryptophan methyl ester (420 mg, prepared in Example (1-b)) in MeOH (6 mL) was added 4N NaOH (2 mL). The mixture was stirred at room temperature for 32 h and evaporated to remove MeOH. To the residue was added 10% aq. citric acid, and the mixture was extracted with chloroform. The organic layer was washed with brine, dried over MgSO$_4$ and evaporated under reduced pressure to give the product (243 mg).

FAB-MS(m/e, $(C_{17}H_{19}N_3O_4+H)^+$): 330

(2-b) Preparation of Boc-DTrp(2-CN)-DNle-OMe

To a mixture of α-N-t-butoxycarbonyl-2-cyano-D-tryptophan (50 mg, prepared in Example (2-a)) and H-DNle-OMe·HCl (30 mg) in dichloromethane (1.5 mL) were added NMM (20 μL), HOBT·H$_2$O (35 mg) and EDCI·HCl (44 mg) under ice-cooling. The mixture was stirred under ice-cooling for 30 min and then at room temperature for 1.5 h. The mixture was diluted with ethyl acetate (20 mL), washed successively with sat. aq. NaHCO$_3$ (20 mL), 10% aq. citric acid (20 mL) and brine (20 mL), dried over MgSO$_4$ and evaporated. The residue was purified by preparative TLC (Merck, Kieselgel 60 F$_{254}$) with chloroform/methanol=30/1 for development to give the product (53.8 mg).

FAB-MS(m/e, $(C_{24}H_{32}N_4O_5+H)^+$): 457

(2-c) Preparation of H-DTrp(2-CN)-DNle-OMe

A solution of Boc-DTrp(2-CN)-DNle-OMe (52 mg, prepared in Example (2-b)) in formic acid (5 mL) was stirred at room temperature for 1 h, and then evaporated. The residue was dissolved in ethyl acetate (60 mL) and the solution was washed with sat. aq. $NaHCO_3$ (30 mL) and brine (30 mL), dried over $MgSO_4$ and evaporated under reduced pressure to give the product (40 mg).

FAB-MS(m/e, $(C_{19}H_{24}N_4O_3+H)^+$): 357

(2-d) Preparation of 2,6-dimethylpiperidinocarbonyl-Val-OH

To a mixture of H-Val-OBzl·TsOH (3.79 g) and CDI (1.78 g) in dry THF (20 mL) was added TEA (1.53 mL) under ice-cooling over a period of 5 min under a nitrogen atmosphere, and then the mixture was stirred at room temperature for 10 min. To the mixture was added 2,6-dimethylpiperidine (1.48 mL) under ice-cooling. The mixture was allowed to warm to room temperature and stirred over night. To the mixture was added water (100 mL), and the mixture was extracted with ethyl acetate (50 mL×3). The combined organic extracts were washed with 1N HCl (50 mL×2), sat. aq. $NaHCO_3$ (50 mL) and brine (50 mL) successively, dried over $MgSO_4$ and evaporated under reduced pressure. The residue was purified by silica gel chromatography (Merck, Kieselgel 60) with ethyl acetate/hexane=2/1 for elution to give 2,6-dimethylpiperidinocarbonyl-Val-OBzl (3.09 g), which was hydrogenated over 10% Pd-C at an atmospheric pressure of hydrogen to give the product (2.20 g) as a colorless amorphous.

FAB-MS(m/e, $(C_{13}H_{24}N_2O_3+H)^+$): 257

(2-e) Preparation of 2,6-dimethylpiperidinocarbonyl-Val-DTrp(2-CN)-DNle-OMe

To a mixture of H-DTrp(2-CN)-DNle-OMe (20 mg, prepared in Example (2-c)) and 2,6-dimethylpiperidinocarbonyl-Val-OH (16 mg, prepared in Example (2-d)) in DMF (0.5 mL) were added HOBT·$H_2O$ (13 mg) and EDCI·HCl (16 mg) under ice-cooling. The mixture was stirred under ice-cooling for 1 h and at room temperature for 2 h. The mixture was diluted with ethyl acetate (60 mL), washed successively with sat. aq. $NaHCO_3$ (30 mL), 10% aq. citric acid (30 mL) and brine (30 mL), dried over $MgSO_4$ and evaporated. The residue was purified by preparative TLC (Merck, Kieselgel 60 $F_{254}$) with chloroform/methanol=20/1 for development to give the product (26.6 mg).

FAB-MS(m/e, $(C_{32}H_{46}N_6O_5+H)^+$): 595

(2-f) Preparation of Compound 1

To a solution of 2,6-dimethylpiperidinocarbonyl-Val-DTrp(2-CN)-DNle-OMe (23 mg, prepared in Example (2-e)) in methanol (1 mL) was added 1N NaOH (0.25 mL) under ice-cooling. The mixture was stirred under ice-cooling for 10 min and then at room temperature for 2 h. After being added water (1 mL), the mixture was evaporated to remove methanol. To the resulting aqueous solution was added 1N HCl under ice-cooling to give a precipitate, which was collected by filtration and dried under reduced pressure to give the title compound (19.1 mg) as colorless crystals.

m.p.: 110°–113° C.

IR(KBr,$cm^{-1}$):
3300,2962,2933,2222,1722,1653,1533,1456,1394,1342, 1126,1072,746,608

High Resolution FAB-MS(m/e, $(C_{31}H_{44}N_6O_5+H)^+$): calcd: 581.3451 found: 581.3426

$^1$H-NMR(300 MHz,DMSO-$d_6$, δ ppm): 0.30(3H,d,J=6.7 Hz),0.58(3H,d,J=6.7 Hz),0.87(3H,t,J= 7.3 Hz),1.04(3H,d,J= 6.5 Hz),1.06(3H,d,J=6.5 Hz),0.83– 1.80(13H,m),3.02(1H, dd,J=9.8 Hz,13.8 Hz),3.45(1H,dd, J=4.2 Hz,13.8 Hz), 3.64(1H,t,J=7.8 Hz),4.00–4.20(3H,m), 4.83(1H,dt,J=4.2 Hz,9.8 Hz),5.91(1H,d,J=7.5 Hz),7.11 (1H,t,J=7.6 Hz), 7.30(1H,t,J=7.6 Hz),7.36(1H,d,J=7.6 Hz),7.81(1H,d,J=7.6 Hz),8.25(1H,d,J=7.3 Hz),8.36(1H,d, J=9.8 Hz),12.02(1H,s)

Each Compound 2–8 described in the following Examples 3–7 was prepared using each corresponding amino acid ester instead of H-Val-OBzl·TsOH which was used in Example (2-d) in the same manner described in Example 2.

EXAMPLE 3

Compound 2
m.p.: 145°–153° C.

IR(KBr,$cm^{-1}$):
3394,2954,2868,2362,2222,1657,1624,1520,1387,1238, 1124,1088,746,679,609

High Resolution FAB-MS(m/e, $(C_{32}H_{46}N_6O_5+H)^+$): calcd: 595.3608 found: 595.3588

$^1$H-NMR(300 MHz,DMSO-$d_6$, δ ppm): 0.64(6H,d,J=5.6 Hz),0.85(3H,t,J=6.9 Hz),1.01(3H,d,J= 7.0 Hz),1.04(3H,d,J= 7.0 Hz),0.71–1.78(15H,m),3.04(1H, dd,J=10.2 Hz,14.5 Hz), 3.42(1H,dd,J=4.2 Hz,14.5 Hz),3.83– 3.95(1H,m), 3.99–4.18(3H,m),4.61–4.73(1H,m),6.04(1H, d,J=6.5 Hz), 7.09(1H,t,J=7.8 Hz),7.29(1H,t,J=7.8 Hz), 7.36(1H,d,J=7.8 Hz),7.80(1H,d,J=7.8 Hz),8.04(1H,d,J= 6.8 Hz),8.23(1H,d, J=9.3 Hz),12.05(1H,s)

EXAMPLE 4

Compound 3
IR(KBr,$cm^{-1}$):
270,2950,2869,2219,1743,1658,1615,1515,1444,1371, 1247,1135,1074,746,609

High Resolution FAB-MS(m/e, $(C_{34}H_{50}N_6O_5+H)^+$): calcd: 623.3921 found: 623.3936

$^1$H-NMR(300 MHz,CDCl$_3$, δ ppm): 0.80(3H,t,J=7.2 Hz), 0.90(9H,s),1.17(3H,d,J=7.1 Hz), 1.18(3H,d,J=7.1 Hz), 1.04–1.82(14H,m),3.49(2H,d,J= 6.7 Hz),3.65(3H,s), 3.94–4.08(1H,m),4.08–4.23(2H,m), 4.38–4.49(1H,m), 4.70(1H,d,J=7.1 Hz),4.80–4.90(1H,m), 6.53(1H,d,J=9.1 Hz),7.14–7.24(2H,m),7.32–7.40(2H,m), 7.79(1H,d,J=8.0 Hz),8.95(1H,s)

Compound 4
m.p.: 158°–164° C.

IR(KBr,$cm^{-1}$):
3388,3303,2954,2869,2221,1722,1658,1619,1529,1388, 1247,1126,1076,746,609

High Resolution FAB-MS(m/e, $(C_{33}H_{48}N_6O_5+H)^+$): calcd: 609.3764 found: 609.3768

$^1$H-NMR(300 MHz,DMSO-$d_6$, δ ppm): 0.75(9H,s), 0.84(3H,t,J=6.7 Hz),1.02(3H,d,J=6.9 Hz), 1.03(3H,d,J=6.9 Hz),0.90–1.85(14H,m),3.06(1H,dd,J= 9.8 Hz,14.4 Hz), 3.20–3.50(2H,m),3.91–4.22(3H,m),4.55– 4.70(1H,m), 6.03(1H,d,J=7.6 Hz),7.08(1H,t,J=7.8 Hz), 7.28(1H,t,J=7.8 Hz),7.36(1H,d,J=7.8 Hz),7.80(1H,d,J= 7.8 Hz),7.94(1H,d, J=5.4 Hz),8.12(1H,d,J=8.7 Hz),12.06 (1H,s)

EXAMPLE 5

Compound 5
m.p.: 146°–152° C.

IR(KBr,$cm^{-1}$):
3305,2964,2937,2873,2221,1720,1660,1621,1525,1388, 1240,1151,1128,748,607

High Resolution FAB-MS(m/e, $(C_{30}H_{42}N_6O_5+H)^+$): calcd: 567.3295 found: 567.3287

$^1$H-NMR(300 MHz,DMSO-$d_6$, δ ppm): 0.27(3H,d,J=6.7 Hz),0.57(3H,d,J=6.7 Hz),0.86(3H,t,J= 37.4 Hz),1.03(3H,d, J=6.8 Hz),1.05(3H,d,J=6.8 Hz),0.80– 1.82(11H,m),3.00(1H, dd,J=10.9 Hz,14.3 Hz),3.46(1H,dd, J=3.9 Hz,14.3 Hz), 3.60(1H,t,J=7.4 Hz),4.01–4.20(3H,m), 4.75–4.88(1H,m), 5.92(1H,d,J=7.4 Hz),7.10(1H,t,J=7.7 Hz),7.28(1H,t,J=7.7

Hz),7.35(1H,d,J=7.7 Hz),7.79(1H, d,J=7.7 Hz),8.24(1H,d, J=7.3 Hz),8.38(1H,d,J=9.6 Hz), 12.02(1H,s),12.41(1H,brs)

EXAMPLE 6

Compound 6
m.p.: 148°–154° C.
IR(KBr,cm$^{-1}$):
3305,2964,2937,2873,2221,1718,1660,1621,1525,1444, 1384,1346,1243,1151,1128,746,607
High Resolution FAB-MS(m/e, $(C_{31}H_{44}N_6O_5+H)^+$): calcd: 581.3451 found: 581.3469
$^1$H-NMR(300 MHz,DMSO-d$_6$, δ ppm): 0.22(3H,d,J=6.8 Hz),0.62(3H,t,J=7.3 Hz),0.85(3H,t,J= 7.2 Hz),1.03(3H,d,J= 7.5 Hz),1.05(3H,d,J=7.5 Hz),0.74– 1.80(13H,m),3.01(1H, dd,J=10.2 Hz,14.5 Hz),3.45(1H,dd, J=4.0 Hz,14.5 Hz), 3.68(1H,t,J=7.6 Hz),4.00–4.20(3H,m), 4.73–4.88(1H,m), 5.94(1H,d,J=7.6 Hz),7.10(1H,t,J=7.6 Hz),7.28(1H,t,J=7.6 Hz),7.35(1H,d,J=7.6 Hz),7.79(1H, d,J=7.6 Hz),8.16(1H,d, J=7.4 Hz),8.38(1H,d,J=9.3 Hz), 12.03(1H,s)

EXAMPLE 7

Compound 7
IR(KBr,cm$^{-1}$):
3288,2944,2869,2221,1743,1660,1619,1521,1442,1382, 1346,1245,1209,1149,748
High Resolution FAB-MS(m/e, $(C_{33}H_{46}N_6O_5+H)^+$): calcd: 607.3608 found: 607.3598
$^1$H-NMR(300 MHz,CDCl$_3$, δ ppm): 0.81(3H,t,J=7.3 Hz), 1.18(3H,d,J=7.1 Hz),1.19(3H,d,J= 7.1 Hz),0.90–1.80(18H, m),1.98–2.15(1H,m),3.40(1H,dd, J=8.6 Hz,14.6 Hz), 3.58(1H,dd,J=5.5 Hz,14.6 Hz),3.65(3H, s),3.88(1H,dd,J= 6.8 Hz,9.3 Hz),3.93–4.10(1H,m),4.10– 4.25(1H,m), 4.40–4.51(1H,m),4.84–4.99(2H,m),6.57(1H, d,J=9.0 Hz), 7.11–7.23(1H,m),7.30–7.40(3H,m),7.77(1H, d,J=8.0 Hz), 9.49(1H,s)
Compound 8
m.p.: 162°–169° C.
IR(KBr,cm$^{-1}$):
3309,2942,2869,2221,1720,1660,1619,1525,1446,1388, 1346,1243,1147,746,607
High Resolution FAB-MS(m/e, $(C_{32}H_{44}N_6O_5+H)^+$): calcd: 593.3451 found: 593.3459
$^1$H-NMR(300 MHz,DMSO-d$_6$, δ ppm): 0.85(3H,t,J=7.2 Hz),1.02(3H,d,J=7.4 Hz),1.05(3H,d,J= 7.4 Hz), 0.55–1.87(19H,m),3.01(1H,dd,J=10.7 Hz,14.4 Hz), 3.46(1H,dd,J=3.9 Hz,14.4 Hz),3.64(1H,t,J=7.2 Hz),3.99– 4.20(3H,m),4.70–4.83(1H,m),6.00(1H,d,J=7.2 Hz),7.10 (1H,t,J=7.7 Hz),7.28(1H,t,J=7.7 Hz),7.36(1H,d,J=7.7 Hz), 7.78(1H,d,J=7.7 Hz),8.08(1H,d,J=6.0 Hz),8.36(1H,d, J=9.6 Hz),12.05(1H,s)

EXAMPLE 8

Synthesis of Compound 9
To a solution of Compound 8 (15 mg, prepared in Example 7) in DMF (1 mL) were added N-hydroxysuccinimide (5 mg) and EDCI·HCl (8 mg) under ice-cooling. The mixture was stirred under ice-cooling for 2 h. To the mixture was added 40% methanolic solution of methylamine (15 μL). After being stirred under ice-cooling for 1 h, the mixture was diluted with water and extracted with ethyl acetate (20 mL). The organic layer was washed with sat. aq. NaHCO$_3$ (10 mL), 10% aq. citric acid (10 mL) and brine (10 mL) successively, dried over MgSO$_4$ and evaporated under reduced pressure to give the title compound (12.6 mg).

IR(KBr,cm$^{-1}$):
3330,2942,2869,2221,1720,1656,1619,1527,1380,1247, 748,607
High Resolution FAB-MS(m/e, $(C_{33}H_{47}N_7O_4+H)^+$): calcd: 606.3768 found: 606.3748
$^1$H-NMR(300 MHz,DMSO-d$_6$, δ ppm): 0.84(3H,t,J=7.3 Hz),1.03(3H,d,J=6.4 Hz),1.05(3H,d,J= 6.4 Hz), 0.58–1.92(19H,m),2.52(3H,d,J=4.6 Hz),3.12(1H, dd,J=10.4 Hz,14.4 Hz),3.43(1H,dd,J=4.2 Hz,14.4 Hz),3.62 (1H,dd,J= 6.3 Hz,9.8 Hz),3.94–4.22(3H,m),4.54–4.68(1H, m),6.25(1H,d,J=6.3 Hz),7.07(1H,d,J=4.6 Hz),7.10(1H,t, J=7.7 Hz),7.29(1H,t,J=7.7 Hz),7.37(1H,d,J=7.7 Hz),7.77 (1H,d,J=7.7 Hz),8.02(1H,d,J=8.6 Hz),8.54(1H,d,J=8.3 Hz), 12.07(1H,S)

EXAMPLE 9

Synthesis of Compounds 10 and 11
(9-a) Preparation of Boc-DTrp(2-CN)-DAsp(OMe)-O$^t$Bu
To a mixture of α-N-t-butoxycarbonyl-2-cyano-D-tryptophan (100 mg, prepared in Example (2-a)) and H-DAsp(OMe)-O$^t$Bu·HCl (80 mg) in DMF (4 mL) were added NMM (37 μL), HOBT·H$_2$O (56 mg) and EDCI·HCl (70 mg) under ice-cooling. The mixture was stirred under ice-cooling for 30 min and at room temperature for 1 h. The mixture was diluted with ethyl acetate (30 mL), washed with sat. aq. NaHCO$_3$ (30 mL), 10% aq. citric acid (30 mL) and brine (30 mL) successively, dried over MgSO$_4$ and evaporated under reduced pressure. The residue was purified by MPLC (Merck, LiChroprep Si 60) with hexane/ethyl acetate=2/1 for elution to give the product (80.7 mg).
FAB-MS(m/e, $(C_{26}H_{34}N_4O_7+H)^+$): 515
(9-b) Preparation of H-DTrp(2-CN)-DAsp(OMe)-O$^t$Bu
A solution of Boc-DTrp(2-CN)-DAsp(OMe)-O$^t$Bu (78 mg, prepared in Example (9-a)) in formic acid (3 mL) was stirred at room temperature for 1 h and evaporated under reduced pressure. The residue was dissolved in ethyl acetate (30 mL), and the solution was washed with sat. aq. NaHCO$_3$ (20 mL×2), dried over MgSO$_4$ and evaporated under reduced pressure to give the product (53 mg).
FAB-MS(m/e, $(C_{21}H_{26}N_4O_5+H)^+$): 415
(9-c) Preparation of α-N-t-butoxycarbonyl-S-methyl-D-penicillamine
To a mixture of D-penicillamine (1.49 g) in ethanol (10 mL) and 1N NaOH (11 mL) was added iodomethane (0.68 mL), and the mixture was stirred at room temperature overnight under argon atmosphere. To the mixture were added di-t-butyl dicarbonate (2.53 mL) and 1N NaOH (11 mL). After being stirred at room temperature for 3 h, the mixture was evaporated under reduced pressure to remove ethanol. The resulting aqueous residue was extracted with diethy ether (30 mL). The aqueous layer was acidified with 10% aq. citric acid and extracted with ethyl acetate (10 mL×3). The combined ethyl acetate extracts were washed with brine (10 mL), dried over MgSO$_4$ and evaporated under reduced pressure to give the product (2.47 g).
FAB-MS(m/e, $(C_{11}H_{21}NO_4S+H)^+$): 264
(9-d) Preparation of Boc-DPen(Me)-Leu-OMe
To a mixture of α-N-t-butoxycarbonyl-S-methyl-D-penicillamine (1.32 g, prepared in Example (9-c)) and H-Leu-OMe·HCl (1.09 g) in dichloromethane (20 mL) were added NMM (0.66 mL), HOBT·H$_2$O (0.92 g) and EDCI·HCl (1.15 g) under ice-cooling. The mixture was stirred under ice-cooling for 1 h and at room temperature over night. The mixture was washed with sat. aq. NaHCO$_3$ (20 mL×2), 10% aq. citric acid (20 mL×2) and brine (20 mL) successively, dried over MgSO$_4$ and evaporated under reduced pressure to give the product (1.75 g).

FAB-MS(m/e, $(C_{18}H_{34}N_2O_5S+H)^+$): 391

(9-e) Preparation of Boc-Pro-DPen(Me)-Leu-OMe

A solution of Boc-DPen(Me)-Leu-OMe (1.75 g, prepared in Example (9-d)) in 4N hydrogen chloride in dioxane (20 mL) was stirred at room temperature for 30 min and evaporated to give a colorless crystalline residue (1.39 g). An aliquot (654 mg) of the residue and Boc-Pro-OH (474 mg) were dissolved in dichloromethane (10 mL). To the mixture were added NMM (0.24 mL), HOBT·H₂O (337 mg) and EDCI·HCl (422 mg) under ice-cooling. The mixture was stirred under ice-cooling for 1 h and at room temperature over night. The mixture was washed with sat. aq. NaHCO₃ (10 mL), 10% aq. citric acid (10 mL) and brine (10 mL) successively, dried over MgSO₄ and evaporated under reduced pressure to give the product (0.95 g) as a colorless amorphous.

FAB-MS(m/e, $(C_{23}H_{41}N_3O_6S+H)^+$): 488

(9-f) Preparation of Boc-Pro-DPen(Me)-Leu-OH

To a solution of Boc-Pro-DPen(Me)-Leu-OMe (0.94 g, prepared in Example (9-e)) in methanol (2.5 mL) was added 1N NaOH (2.5 mL) under ice-cooling. The mixture was stirred under ice-cooling for 30 min and at room temperature for 1 h. The mixture was evaporated under reduced pressure to remove methanol and water (20 mL) was added to the residue. The mixture was extracted with diethyl ether (20 mL). The aqueous layer was acidified with 10% aq. citric acid and extracted with ethyl acetate (10 mL×3). The combined ethyl acetate extracts were washed with brine (10 mL), dried over MgSO₄ and evaporated under reduced pressure to give the product (0.94 g).

FAB-MS(m/e, $(C_{22}H_{39}N_3O_6S+H)^+$): 474

(9-g) Preparation of Boc-Pro-DPen(Me)-Leu-DTrp(2-CN)-DAsp(OMe)-O$^t$Bu

To a mixture of H-DTrp(2-CN)-DAsp(OMe)-O$^t$Bu (26 mg, prepared in Example (9-b)) and Boc-Pro-DPen(Me)-Leu-OH (33 mg, prepared in Example (9-f)) in DMF (3 mL) were added HOBT·H₂O (12 mg) and EDCI·HCl (15 mg) under ice-cooling. The mixture was stirred under ice-cooling for 1 h and at room temperature for 1.5 h. The mixture was diluted with ethyl acetate (30 mL), washed with sat. aq. NaHCO₃ (15 mL), 10% aq. citric acid (15 mL) and brine (15 mL) successively, dried over MgSO₄ and evaporated under reduced pressure. The residue was purified by preparative TLC (Merck, Kieselgel 60 F$_{254}$) with chloroform/methanol= 30/1 for development to give the product (42 mg).

FAB-MS(m/e, $(C_{43}H_{46}N_7O_{10}S+H)^+$): 474

(9-h) Preparation of Compound 10

A solution of Boc-Pro-DPen(Me)-Leu-DTrp(2-CN)-DAsp(OMe)-O$^t$Bu (39 mg, prepared in Example (9-g)) in TFA (3 mL) was stirred at room temperature for 1.5 h. After removal of TFA by evaporation, the resulting residue was dissolved in DMF (2 mL) and neutralized by addition of NMM. The mixture was added to a mixture of HOBT·H₂O (11 mg) and EDCI·HCl (14 mg) in DMF (3.5 mL) under ice-cooling over a period of 15 min. After being stirred at 4° C. for 3 days, the mixture was concentrated under reduced pressure. The residue was taken up into ethyl acetate (30 mL), and the mixture was washed with sat. aq. NaHCO₃ (30 mL), 10% aq. citric acid (30 mL) and brine (30 mL) successively, dried over MgSO₄ and evaporated under reduced pressure. The residue was purified by preparative TLC (Merck, Kieselgel 60 F$_{254}$) with hexane/ethyl acetate=1/3 for development to give the title compound (16.4 mg).

IR(KBr,cm$^{-1}$):
3291,3054,2958,2221,1731,1654,1537,1438,1371,1301, 1241,1083,748,607

High Resolution FAB-MS(m/e, $(C_{34}H_{45}N_7O_7S+H)^+$): calcd: 696.3179 found: 696.3194

$^1$H-NMR(300 MHz,CDCl₃, δ ppm): 0.80(3H,d,J=6.4 Hz), 0.85(3H,d,J=6.4 Hz),1.26(3H,s), 1.31(3H,s),1.20–2.10(6H, m),2.06(3H,s),2.29(1H,dd, J=3.6 Hz,16.5 Hz), 2.38–2.50(1H,m),2.74(1H,dd,J=9.9 Hz, 16.5 Hz), 3.30–3.70(4H,m),3.64(3H,s),3.91–4.02(1H,m), 4.42(1H,d, J=10.1 Hz,),4.82(1H,d,J=7.0 Hz),4.78–4.94 (1H,m), 5.02–5.22(1H,m),6.36(1H,d,J=8.7 Hz),6.55(1H,d, J=4.5 Hz),7.16–7.29(1H,m),7.32(1H,d,J=8.3 Hz),7.35– 7.45(2H, m),7.75(1H,d,J=8.3 Hz),8.14(1H,d,J=10.1 Hz), 8.83(1H,s)

(9-i) Preparation of Compound 11

To a solution of Compound 10 (12.4 mg, prepared in Example (9-h)) in methanol (1 mL) was added 1N NaOH (0.5 mL) under ice-cooling. The mixture was allowed to warm to room temperature and stirred for 1.5 h. The mixture was evaporated to remove methanol, and 1N HCl was added to the residue to give a precipitate, which was collected by filtration and dried under reduced pressure to give the title compound (8.1 mg) as a colorless powder.

m.p.: 191°–198° C.

IR(KBr,cm$^{-1}$):
3423,3291,2960,2221,1652,1540,1438,1388,1240,1081, 748,607

High Resolution FAB-MS(m/e, $(C_{33}H_{43}N_7O_7S+H)^+$): calcd: 682.3023 found: 682.3047

$^1$H-NMR(300 MHz,DMSO-d₆, δ ppm): 0.56(3H,d,J=5.8 Hz),0.58(3H,d,J=5.8 Hz),0.88–1.28(3H, m),1.17(3H,s), 1.22(3H,s),1.62–1.82(2H,m),1.82–2.05 (1H,m),2.00(3H,s), 2.20–2.31(1H,m),2.35(1H,dd,J=3.4 Hz,16.4 Hz),2.83(1H, dd,J=10.5 Hz,16.4 Hz),3.02–3.25(3H, m),3.44(1H,dd,J=4.0 Hz,14.5 Hz),3.88–4.01(1H,m),4.43– 4.58(1H,m),4.50(1H,d, J=10.6 Hz,),4.77(1H,d,J=6.8 Hz), 4.88–5.01(1H,m), 7.09(1H,t,J=7.8 Hz),7.30(1H,t,J=7.8 Hz),7.38(1H,d,J=7.8 Hz),7.66(1H,d,J=9.0 Hz),7.77(1H, d,J=7.8 Hz),7.81(1H,d, J=10.6 Hz),8.92(1H,d,J=6.7 Hz), 8.95(1H,d,J=9.2 Hz), 12.10(1H,s),12.37(1H,brs)

EXAMPLE 10

Synthesis of Compound 12

Compound 12 was prepared using DVal instead of D-penicillamine which was used in Example (9-c) in the same manner described in Example 9.

m.p.: 168°–171° C.

IR(KBr,cm$^{-1}$):
3457,3296,2960,2929,2222,1659,1593,1340,1080,754,604

High Resolution FAB-MS(m/e, $(C_{32}H_{41}N_7O_7+H)^+$): calcd: 636.3146 found: 636.3163

$^1$H-NMR(300 MHz,DMSO-d₆, δ ppm): 0.56(3H,d,J=6.3 Hz),0.57(3H,d,J=6.3 Hz),0.82(3H,d,J= 6.7 Hz),0.85(3H,d, J=6.7 Hz),1.03–2.29(8H,m),2.40(1H, dd,J=4.0 Hz,16.4 Hz), 2.83(1H,dd,J=10.0 Hz,16.4 Hz),3.17 (1H,dd,J=10.5 Hz,14.4 Hz),3.48(1H,dd,J=8.9 Hz,14.4 Hz), 3.28–3.46(2H,m), 3.90–4.00(1H,m),4.14(1H,dd,J=7.7 Hz, 9.9 Hz), 4.51–4.59(1H,m),4.77(1H,d,J=7.5 Hz),4.95(1H, dt,J=4.0 Hz,10.0 Hz),7.11(1H,t,J=7.8 Hz),7.32(1H,t,J= 7.8 Hz), 7.39(1H,d,J=7.8 Hz),7.51(1H,d,J=9.9 Hz),7.76– 7.82(2H, m),8.78(1H,d,J=5.1 Hz),8.89(1H,d,J=9.0 Hz), 12.11(1H,s).

We claim:

1. A peptide derivative of the formula:

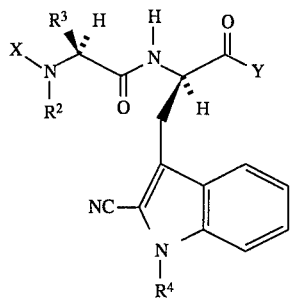

wherein $R^2$ is a hydrogen atom or a lower alkyl group; $R^3$ is a lower alkyl group which is unsubstituted or substituted with a lower alkylthio group, a lower alkenyl group, a cycloalkyl group or a cycloalkyl lower alkyl group wherein optional one to four hydrogen atoms on the ring may independently be replaced by a lower alkyl group, an aryl group, a heteroaryl group, an aryl lower alkyl group or a heteroaryl lower alkyl group; $R^4$ is a hydrogen atom, a lower alkyl group or an acyl group; X and Y are mutually dependent; when X is a group of the formula $R^{11}$—O—C(=O) or a group of the formula $R^{12}R^{13}N$—C(=O), Y is a group of the formula:

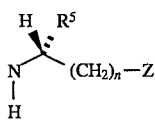

wherein $R^{11}$ is a lower alkyl group or an aryl group, $R^{12}$ is a lower alkyl group, a cycloalkyl group, a cycloalkyl lower alkyl group, a 1-adamantyl group, or an aryl group or a heteroaryl group wherein optional one or two hydrogen atoms on the ring may independently be replaced by an optional group selected from the group consisting of a lower alkyl group, a lower alkoxy group, a halogen atom, a trifluoromethyl group, a nitro group, an amino group and a formyl amino group, $R^{13}$ is a hydrogen atom, a lower alkyl group which is unsubstituted or substituted with a hydroxyl group, a cycloalkyl group or a cycloalkyl lower alkyl group, or $R^{12}$ and $R^{13}$ form, together with the adjacent nitrogen atom, a 5- to 9-membered nitrogen-containing saturated heterocyclic ring having 4 to 8 carbon atoms (wherein among methylene groups forming the ring, optional one methylene group may be replaced by a thio group, optional one to four hydrogen atoms on the carbon atoms of the heterocyclic ring may independently be replaced by a lower alkyl group or a hydroxy lower alkyl group, and further two adjacent carbon atoms in the heterocyclic ring may form a benzo fused ring), $R^5$ is a hydrogen atom, or a lower alkyl group or a lower alkenyl group which may have one to three substituents selected from the group consisting of a hydroxyl group, a lower alkoxy group, a lower alkylthio group, an aryl group and a heteroaryl group, n is 0 or 1, Z is a hydroxymethyl group, a group of the formula $CO_2R^{61}$ (wherein $R^{61}$ is a hydrogen atom or a lower alkyl group), a group of the formula $CONR^{62}R^{63}$ (wherein each of $R^{62}$ and $R^{63}$ is independently a hydrogen atom, an aryl group, a heteroaryl group, or a lower alkyl group which may have one to three substituents selected from the group consisting of a hydroxyl group, a carboxyl group and a sulfo group), a 1H-tetrazol-5-yl group, a sulfo group or a phosphono group, and when X is a group of the formula:

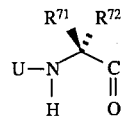

, Y is a group of the formula:

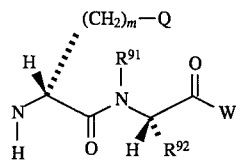

wherein $R^{71}$ is a hydrogen atom, $R^{72}$ is a lower alkyl group which is unsubstituted or substituted with a lower alkylthio group, a cycloalkyl group, an aryl group or a heteroaryl group, or $R^{71}$ and $R^{72}$ together form an alkylene group having 2 to 5 carbon atoms, m is 0, 1 or 2, Q is a group of the formula $COOR^8$ (wherein $R^8$ is a hydrogen atom or a lower alkyl group), a sulfo group or a 1H-tetrazol-5-yl group, each of $R^{91}$ and $R^{92}$ is independently a hydrogen atom, or a lower alkyl group or a lower alkenyl group which may have one to three substituents selected from the group consisting of a hydroxyl group, a lower alkoxy group, a mercapto group, a lower alkylthio group, a carboxyl group, a carbamoyl group, an amino group, a guanidino group, an aryl group and a heteroaryl group, or $R^{91}$ and $R^{92}$ together form an alkylene group having 2 to 4 carbon atoms wherein optional one hydrogen atom in the alkylene group may be replaced by a hydroxyl group, and one sulfur atom may be present, and U and W together form a single bond; or a pharmaceutically acceptable salt thereof.

2. The peptide derivative or a pharmaceutically acceptable salt thereof according to claim 1, wherein X is a group of the formula $R^{11}$—O—C(=O) or a group of the formula $R^{12}R^{13}N$—C(=O), and Y is a group of the formula:

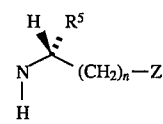

wherein $R^{11}$, $R^{12}$, $R^{13}$, $R^5$, n and Z are as defined in claim 1.

3. The peptide derivative or a pharmaceutically acceptable salt thereof according to claim 1, wherein X is a group of the formula:

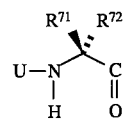

and Y is a group of the formula:

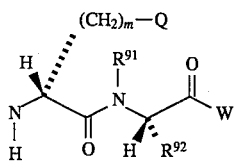

wherein $R^{71}$, $R^{72}$, U, $R^{91}$, $R^{92}$, m, Q and W are as defined in claim 1.

4. The peptide derivative or a pharmaceutically acceptable salt thereof according to claim 1, wherein $R^2$ is a hydrogen atom; $R^3$ is a lower alkyl group which is unsubstituted or substituted with a lower alkylthio group, or a cycloalkyl group or a cycloalkyl lower alkyl group wherein optional one or two hydrogen atoms on the ring may independently be replaced by a lower alkyl group; $R^4$ is a hydrogen atom or a lower alkyl group; X is a group of the formula $R^{12}R^{13}N-C(=O)$, Y is a group of the formula:

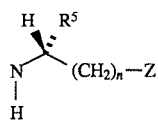
(II)

wherein $R^{12}$ is a lower alkyl group, a cycloalkyl group, a cycloalkyl lower alkyl group, or an aryl group wherein optional one or two hydrogen atoms on the ring may independently be replaced by an optional group selected from the group consisting of a lower alkyl group, a halogen atom, a trifluoromethyl group and a nitro group, $R^{13}$ is a hydrogen atom, a lower alkyl group, a cycloalkyl group or a cycloalkyl lower alkyl group, or $R^{12}$ and $R^{13}$ form, together with the adjacent nitrogen atom, a 5- to 7- membered nitrogen-containing saturated heterocyclic ring having 4 to 7 carbon atoms (wherein among methylene groups forming the ring, optional one methylene group not adjacent to the above nitrogen atom may be replaced by a thio group, and further optional one to four hydrogen atoms on the carbon atoms of the heterocyclic ring may independently be replaced by a lower alkyl group); $R^5$ is a lower alkyl group which may have one or two substituents selected from the group consisting of a lower alkylthio group, an aryl group and a heteroaryl group; n is 0 or 1; and Z is a group of the formula $CO_2R^{61}$ (wherein $R^{61}$ is a hydrogen atom or a lower alkyl group), a group of the formula $CONHR^{62}$ (wherein $R^{62}$ is a hydrogen atom or a lower alkyl group), a 1H-tetrazol-5-yl group or a sulfo group.

5. The peptide derivative or a pharmaceutically acceptable salt thereof according to claim 1, wherein $R^2$ is a hydrogen atom; $R^3$ is a lower alkyl group which is unsubstituted or substituted with a lower alkylthio group, or a cycloalkyl group or a cycloalkyl lower alkyl group wherein optional one or two hydrogen atoms on the ring may independently be replaced by a lower alkyl group; $R^4$ is a hydrogen atom or a lower alkyl group; X is a group of the formula:

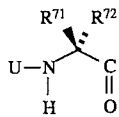
(III)

and Y is a group of the formula:

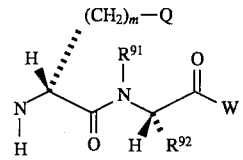
(IV)

wherein $R^{71}$ is a hydrogen atom; $R^{72}$ is a lower alkyl group which is unsubstituted or substituted by a lower alkylthio group, or $R^{71}$ and $R^{72}$ together form an alkylene group having 2 to 5 carbon atoms; m is 0, 1 or 2; Q is a group of the formula $COOR^8$ (wherein $R^8$ is a hydrogen atom or a lower alkyl group), a sulfo group or a 1H-tetrazol-5-yl group; $R^{91}$ is a lower alkyl group, $R^{92}$ is a hydrogen atom, or a lower alkyl group which may have substituents selected from the group consisting of a hydroxyl group, a mercapto group, a lower alkylthio group, a carboxyl group, a carbamoyl group, an amino group, a guanidino group, an aryl group and a heteroaryl group, or $R^{91}$ and $R^{92}$ together form an alkylene group having 2 to 4 carbon atoms wherein optional one hydrogen atom in the alkylene group may be replaced by a hydroxyl group, and one sulfur atom may be present; and U and W together form a single bond.

6. The peptide derivative or a pharmaceutically acceptable salt thereof according to claim 1, wherein $R^2$ is a hydrogen atom; $R^3$ is a lower alkyl group or a cycloalkyl group; $R^4$ is a hydrogen atom; X is a group of the formula $R^{12}R^{13}N-C(=O)$; Y is a group of the formula:

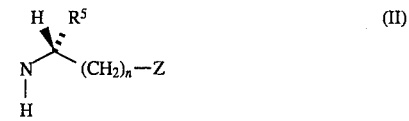
(II)

wherein $R^{12}$ and $R^{13}$ form, together with the adjacent nitrogen atom, a 5-to 7- membered nitorgen-containing saturated heterocyclic ring having 4 to 7 carbon atoms (wherein optional one to four hydrogen atoms on the carbon atoms of the geterocyclic ring may independently be replaced by a lower alkyl group); $R^5$ is a lower alkyl group; n is 0; and Z is a group of the formula $CO_2R^{61}$ (wherein $R^{61}$ is a hydrogen atom or a lower alkyl group) or a group of the formula $CONHR^{62}$ (wherein $R^{62}$ is a o hydrogen atom or a lower alkyl group).

7. The peptide derivative or a pharmaceutically acceptable salt thereof according to claim 1, wherein $R^2$ is a hydrogen atom; $R^3$ is a lower alkyl group or a cycloalkyl group; $R^4$ is a hydrogen atom; X is a group of the formula:

(III)

and Y is a group of the formula:

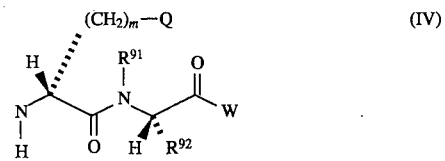
(IV)

wherein $R^{71}$ is a hydrogen atom; $R^{72}$ is a lower alkyl group which is unsubstituted or substituted by a lower alkylthio group; m is 1; Q is a group of the formula $COOR^8$ (wherein $R^8$ is a hydrogen atom or a lower alkyl group); $R^{91}$ and $R^{92}$ together form an alkylene group having 2 to 4 carbon atoms ; and U and W together form a single bond.

8. An endothelin antagonistic agent comprising an effective amount of a peptide derivative of the formula (I) as defined in claim 1 or a pharmaceutically acceptable salt thereof, and a pharmaceutically acceptable carrier.

* * * * *